US009545342B2

(12) United States Patent
Cretu-Petra

(10) Patent No.: US 9,545,342 B2
(45) Date of Patent: Jan. 17, 2017

(54) MULTIFUNCTIONAL MEDICAL MONITORING SYSTEM

(71) Applicant: EM Medical LLC, Vancouver (CA)

(72) Inventor: Eugen Cretu-Petra, Dandenong (AU)

(73) Assignee: FIT ASSIST MEDICAL INC., Vancouver (CA)

(*) Notice: Subject to any disclaimer, the term of this patent is extended or adjusted under 35 U.S.C. 154(b) by 0 days.

(21) Appl. No.: 14/278,261

(22) Filed: May 15, 2014

(65) Prior Publication Data

US 2014/0266736 A1 Sep. 18, 2014

Related U.S. Application Data

(63) Continuation-in-part of application No. 12/877,115, filed on Sep. 8, 2010.

(51) Int. Cl.

| | |
|---|---|
| ***A61F 13/42*** | (2006.01) |
| ***A61B 5/00*** | (2006.01) |
| ***A61B 5/01*** | (2006.01) |

(52) U.S. Cl.

CPC ................. *A61F 13/42* (2013.01); *A61B 5/01* (2013.01); *A61B 5/6801* (2013.01); *A61B 5/6802* (2013.01); *A61B 5/6808* (2013.01); *A61F 2013/421* (2013.01); *A61F 2013/424* (2013.01)

(58) Field of Classification Search

CPC ......... A61B 5/002; A61B 5/0002; A61B 5/01; A61B 5/015; A61B 5/1113; A61B 5/6801–5/6844; A61B 5/6892; A61F 13/42; A61F 2013/42; A61F 2013/421–2013/429; G06F 19/3418

See application file for complete search history.

(56) References Cited

U.S. PATENT DOCUMENTS

| | | | | |
|---|---|---|---|---|
| 4,106,001 A | | 8/1978 | Mahoney | |
| 4,205,672 A | | 6/1980 | Dvorak | |
| 4,800,370 A | * | 1/1989 | Vetecnik | 340/573.5 |
| 5,036,859 A | | 8/1991 | Brown | |

(Continued)

FOREIGN PATENT DOCUMENTS

| | | |
|---|---|---|
| AU | 2009202482 A1 | 1/2010 |
| WO | 2007128038 A1 | 11/2007 |

OTHER PUBLICATIONS

International Search Report for PCT/CA2015/050426 dated Jul. 24, 2015.

*Primary Examiner* — Amine Benlagsir
*Assistant Examiner* — Orlando Bousono
(74) *Attorney, Agent, or Firm* — Bruce M. Green; Oyen Wiggs Green & Mutala LLP

(57) ABSTRACT

A system for monitoring one or more patients has: i) a number of temperature sensors for attachment to the outer surface of an absorbent article at spaced locations for generating a number of signals indicative of the temperature measurements at such locations; ii) a transmitter for communicating the signals to a processor; iii) wherein the processor is provided with computer code which, when executed, determines whether a urination or defecation event has occurred in the absorbent article based on the temperature measurements; and iv) a display for displaying the urination or defecation event to a care-giver. An accelerometer can also be used to provide additional information of use to the caregiver in combination with incontinence information.

16 Claims, 28 Drawing Sheets

(56) References Cited

U.S. PATENT DOCUMENTS

| | | | | |
|---|---|---|---|---|
| 5,144,284 | A * | 9/1992 | Hammett | 340/573.1 |
| 5,266,928 | A | 11/1993 | Johnson | |
| 5,459,452 | A * | 10/1995 | DePonte | 340/573.5 |
| 5,537,095 | A | 7/1996 | Dick et al. | |
| 5,709,222 | A | 1/1998 | Davallou | |
| 5,838,240 | A | 11/1998 | Johnson | |
| 5,903,222 | A | 5/1999 | Kawarizadeh et al. | |
| 6,097,297 | A | 8/2000 | Fard | |
| 6,384,728 | B1 | 5/2002 | Kanor et al. | |
| 6,544,200 | B1 * | 4/2003 | Smith et al. | 600/595 |
| 6,570,053 | B2 | 5/2003 | Roe et al. | |
| 6,573,837 | B2 | 6/2003 | Bluteau | |
| 6,583,722 | B2 | 6/2003 | Juetter et al. | |
| 6,603,403 | B2 | 8/2003 | Juetter et al. | |
| 6,677,859 | B1 | 1/2004 | Bensen | |
| 6,774,800 | B2 | 8/2004 | Friedman et al. | |
| 6,791,460 | B2 | 9/2004 | Dixon et al. | |
| 6,843,766 | B1 | 1/2005 | Nemir et al. | |
| 7,053,781 | B1 | 5/2006 | Haire et al. | |
| 7,127,370 | B2 | 10/2006 | Kelly, Jr. et al. | |
| 7,250,547 | B1 | 7/2007 | Hofmeister et al. | |
| 7,295,125 | B2 | 11/2007 | Gabriel | |
| 7,355,090 | B2 | 4/2008 | Ales, III et al. | |
| 7,449,614 | B2 | 11/2008 | Ales, III | |
| 7,498,478 | B2 | 3/2009 | Long et al. | |
| 7,502,498 | B2 | 3/2009 | Wen et al. | |
| 7,666,151 | B2 | 2/2010 | Sullivan et al. | |
| 7,700,821 | B2 | 4/2010 | Ales, III et al. | |
| 7,733,233 | B2 | 6/2010 | O'Shea et al. | |
| 7,977,529 | B2 | 7/2011 | Bergman et al. | |
| 8,190,452 | B2 | 5/2012 | Vasko et al. | |
| 8,408,041 | B2 | 4/2013 | Ten Kate et al. | |
| 8,416,088 | B2 | 4/2013 | Ortega et al. | |
| 8,421,636 | B2 | 4/2013 | Collette et al. | |
| 8,471,697 | B2 | 6/2013 | Judy et al. | |
| 2002/0003478 | A1 | 1/2002 | Zhao et al. | |
| 2002/0103674 | A1 * | 8/2002 | Reeder et al. | 705/3 |
| 2002/0124295 | A1 * | 9/2002 | Fenwick et al. | 2/69 |
| 2003/0130631 | A1 * | 7/2003 | Springer et al. | 604/361 |
| 2003/0137425 | A1 * | 7/2003 | Gabriel | 340/573.5 |
| 2004/0111045 | A1 * | 6/2004 | Sullivan et al. | 600/595 |
| 2004/0183681 | A1 * | 9/2004 | Smith | 340/573.1 |
| 2004/0220538 | A1 | 11/2004 | Panopoulos | |
| 2005/0033250 | A1 * | 2/2005 | Collette et al. | 604/361 |
| 2005/0046578 | A1 | 3/2005 | Pires | |
| 2005/0099294 | A1 * | 5/2005 | Bogner et al. | 340/540 |
| 2005/0168341 | A1 * | 8/2005 | Reeder et al. | 340/573.1 |
| 2005/0190062 | A1 * | 9/2005 | Sullivan et al. | 340/573.1 |
| 2005/0195085 | A1 | 9/2005 | Cretu-Petra | |
| 2005/0245839 | A1 * | 11/2005 | Stivoric | G06F 19/3418<br>600/549 |
| 2007/0001863 | A1 * | 1/2007 | Gabriel | 340/604 |
| 2007/0156031 | A1 * | 7/2007 | Sullivan et al. | 600/300 |
| 2007/0204691 | A1 | 9/2007 | Bogner et al. | |
| 2007/0233026 | A1 * | 10/2007 | Roe et al. | 604/361 |
| 2007/0287971 | A1 * | 12/2007 | Roe et al. | 604/361 |
| 2008/0036614 | A1 * | 2/2008 | Gabriel | 340/604 |
| 2008/0042858 | A1 * | 2/2008 | Gabriel | 340/604 |
| 2008/0122638 | A1 * | 5/2008 | Gabriel | 340/604 |
| 2008/0122639 | A1 * | 5/2008 | Gabriel | 340/604 |
| 2008/0129519 | A1 * | 6/2008 | Gabriel | 340/573.5 |
| 2008/0169931 | A1 * | 7/2008 | Gentry et al. | 340/573.1 |
| 2008/0255528 | A1 * | 10/2008 | Springer et al. | 604/361 |
| 2008/0272918 | A1 * | 11/2008 | Ingersoll | 340/573.1 |
| 2008/0278336 | A1 * | 11/2008 | Ortega et al. | 340/573.5 |
| 2009/0096615 | A1 * | 4/2009 | Reeder et al. | 340/573.4 |
| 2009/0326340 | A1 * | 12/2009 | Wang et al. | 600/301 |
| 2010/0052917 | A1 * | 3/2010 | Sullivan et al. | 340/573.4 |
| 2010/0073180 | A1 * | 3/2010 | Greene | 340/666 |
| 2010/0141397 | A1 * | 6/2010 | Kim et al. | 340/10.5 |
| 2010/0280472 | A1 * | 11/2010 | Takeuchi et al. | 604/367 |
| 2011/0133935 | A1 * | 6/2011 | Beltmann et al. | 340/573.1 |
| 2012/0059927 | A1 * | 3/2012 | Schieffelin et al. | 709/224 |
| 2014/0121473 | A1 | 5/2014 | Banet et al. | |

* cited by examiner

Guardian - Admin

| First name | Last name | Birth date | Location | Comments | Monitor |
|---|---|---|---|---|---|
| jeanne | Doe | 11/16/2012 | bed 3 | | monitor1 |
| joanne | Doe | 11/17/1948 | bed 2 | | monitor2 |
| john | Doe | 11/16/2012 | bed 1 | | |

FIG. 22
Guardian - Admin
Welc
Patient
Assistant
Start date
End date
p2 p2
11/25/2012
11/25/2012
Generate
Alarms Report
Patient: p2 p2
Start date: 11/25/2012
End date: 11/25/2012
Report date:
11/30/2012
Patient
Assistant
Option
Value
Alarm date
Response date
p2 p2
a1
Position LD
11/25/2012 9:02:07 PM
11/25/2012 9:02:07 PM
p2 p2
a1
Position LD
11/25/2012 6:59:08 PM
11/25/2012 6:59:08 PM
p2 p2
a1
Position RS
11/25/2012 6:58:56 PM
11/25/2012 6:58:56 PM
p2 p2
a1
Air Hot Temperature
95 °F
11/25/2012 11:54:43 AM
11/25/2012 6:54:43 PM
Total
4 alarms
Page 1 of 1

FIG. 30
Welc
Guardian - Admin
Administrators
Doctors
Assistants
Patients
Monitors
Alarms report
Alarm delays report
Work repartition report
Alarm frequency report
Assistant
Patient
Start date
End date
a1
p2 p2
11/25/2012
11/25/2012
Generate
1
of 1
Assistant: a1
Patient: p2 p2
Start date: 11/25/2012
End date: 11/25/2012
Alarm delays report
Report date:
11/30/2012
Assistant
Patient
Option
Value
Alarm Date
Response Date
Delay
a1
p2 p2
Position LD
11/25/2012 9:02:07 PM
11/25/2012 9:02:07 PM
0 min
Position LD
11/25/2012 6:59:08 PM
11/25/2012 7:04:33 PM
5 min
Position RS
11/25/2012 6:58:56 PM
11/25/2012 7:04:33 PM
5 min
Air Hot Temperature
95 °F
11/25/2012 11:54:43 AM
11/25/2012 6:58:43 PM
4 min
Total patient
14 min
Total assistant
14 min
Total
14 min
Page 1 of 1

MULTIFUNCTIONAL MEDICAL MONITORING SYSTEM

REFERENCE TO RELATED APPLICATION

This application is a continuation-in-part under 35 U.S.C. §120, of U.S. application Ser. No. 12/877,115 filed Sep. 8, 2010 entitled "Multifunctional Wireless Intelligent Monitor", which is incorporated herein by this reference.

TECHNICAL FIELD

The invention relates to monitoring systems for monitoring various functions of patients in nursing homes, hospitals or home care.

BACKGROUND

It is important in many situations for medical staff, parents or attendants to be able to monitor the bodily conditions of a patient, infant or elderly person. For example, a nurse will want to know if a patient has stopped breathing or moving, or has fallen down. The cause of that condition could be an accident or an internal condition such as stroke, heart attack, diabetic condition etc. which could be fatal if there is no immediate care. It may also be important to know if there is wetness in the patient's diaper and whether it has been soiled, whether a patient with wounds has been regularly turned, whether the patient's body temperature exceeds a certain value and if the environmental temperature is in a normal comfortable range. The position or orientation of the patient or infant in bed, if he or she stands up, or lays down, how much he or she moved in bed or standing up, how many steps were taken and how long they were, what is the oxygen concentration in his or her blood, pulse and blood pressure—these are all factors which may be significant to the health care attendant. The problem of an elderly patient or infant wandering is similarly of high significance. In that case it is important for the care-giver to know where infant or patient is at any moment, when he/she stood up and started walking or running, and through which door the patient passed. If the patient went out of the facility it is important to know his/her global position.

Existing monitoring systems do not permit a nurse, care-giver or attendant to monitor all of these factors through one interface. Separate diaper wetness monitors which detect wetness, separate temperature monitors or oxygen and pulse monitors or blood pressure monitors are known but not integrated. Existing systems generally do not monitor patient positions nor issue an alarm and record if the patient does not move at all, falls, arouses, if the patient sits or moves, when that happened and how much movement there was. Nor do existing systems monitor how many times a patient or infant urinates or defecates. They do not monitor and record how many steps and what speed or direction a patient took and distance walked, nor detection of the doors a patient went through, or exact location in a building or global positioning. There is therefore also a need for a monitoring system which can detect, monitor and report multiple events and conditions such as the foregoing to a single interface.

Various systems are known for monitoring the diapers of infants or incontinent patients in health care facilities to detect urination or defecation. U.S. Pat. No. 5,903,222 to Kawarizadeh et al. discloses a detector for detecting wetness conditions in diapers using a capacitive sensor in a housing attached to the exterior surface of the garment being monitored. If a wetness condition is detected a signal is transmitted to a central monitoring station. U.S. Pat. No. 6,570,053 to Roe et al. discloses a diaper which has an electrical sensor to detect signals that correlate to an impending elimination of bodily waste. U.S. Pat. No. 7,977,529 to Bergman et al. discloses an incontinence management system for monitoring wetness events in the diapers of multiple patients. The sensors in such system are located within the diaper so the diapers in such system are designed for use for only a few days as the sensors only last for one incontinent event. The present inventor has also disclosed in United States published patent application Publication no. 2005/0195085 a wireless monitoring system having a number of sensors which attach to a diaper.

A problem with previous systems is that their useful life is limited to detecting only one urination or defecation event. Since typically such monitors use sensors that are inside the diaper, once the diaper is wet or soiled, for example, subsequent events cannot be detected. There is therefore a need for a monitoring system in which the diaper is useful for more than one incontinence event. There is also a need for a monitoring system which can detect, monitor and report multiple events of urination or defecation without the diaper or other garment having been changed. There is a further need for a system in which the attendant can determine how many incontinence events have occurred in the diaper, the volume of such events, how long since the last event and how frequent the events are. There is a further need for systems for monitoring incontinence which can be used in wound management.

The foregoing examples of the related art and limitations related thereto are intended to be illustrative and not exclusive. Other limitations of the related art will become apparent to those of skill in the art upon a reading of the specification and a study of the drawings.

SUMMARY

The following embodiments and aspects thereof are described and illustrated in conjunction with systems, tools and methods which are meant to be exemplary and illustrative, not limiting in scope. In various embodiments, one or more of the above-described problems have been reduced or eliminated, while other embodiments are directed to other improvements.

There is provided a monitoring system which can detect, monitor and report multiple events of urination or defecation without the diaper or other garment having been changed. More particularly the need for a transducer or sensor which must stay inside diaper which, once it becomes wet or soiled cannot detect a second soilness/wetness is avoided. Temperature variations are measured on the diaper surface. Sensor variations are interpreted by an intelligent processor suitably programmed with software to detect and measure more than one urination or defecation event in the same diaper.

Further an embodiment may also provide an accelerometer and related software working with the same processor to make possible more accurate detection of incontinence events and also possibly patient turn-check as part of wound management, fall, position or orientation and motion. Secondary detectors may measure body temperature, air temperature, oxygen concentration in the blood and blood pressure or other variables or characteristics. The system links sensors, interfaces and care-giver pagers or smartphones by Wi-Fi through a central computer to co-ordinate processing and recordal of data from multiple patients.

Embodiments therefore provide a system for monitoring multiple patients to an individually determined standard of institutional or home care, for incontinence, wound management, patient location for wandering or falls. The system may include a portable and reusable multi-sensory device, wherein all sensors are on the external surface of the diaper or the patient's skin and thus are reusable. The device may be attached on each patient with wireless connection to a nurse pager by RF signal or to a server through a Wi-Fi, GPS and GPRS interface. This server may allow monitoring on terminals or caregivers' portable devices such as mobile phone or tablet to receive and record alarms for immediate attention, and other data for future analysis for one or multiple patients. The system increases the quality of care for one patient in home care or multiple patients while allowing the caregiver to reduce costs.

In addition to the exemplary aspects and embodiments described above, further aspects and embodiments will become apparent by reference to the drawings and by study of the following detailed descriptions.

BRIEF DESCRIPTION OF DRAWINGS

Exemplary embodiments are illustrated in referenced figures of the drawings. It is intended that the embodiments and figures disclosed herein are to be considered illustrative rather than restrictive.

DESCRIPTION

Throughout the following description specific details are set forth in order to provide a more thorough understanding to persons skilled in the art. However, well known elements may not have been shown or described in detail to avoid unnecessarily obscuring the disclosure. Accordingly, the description and drawings are to be regarded in an illustrative, rather than a restrictive, sense.

Figure 1:
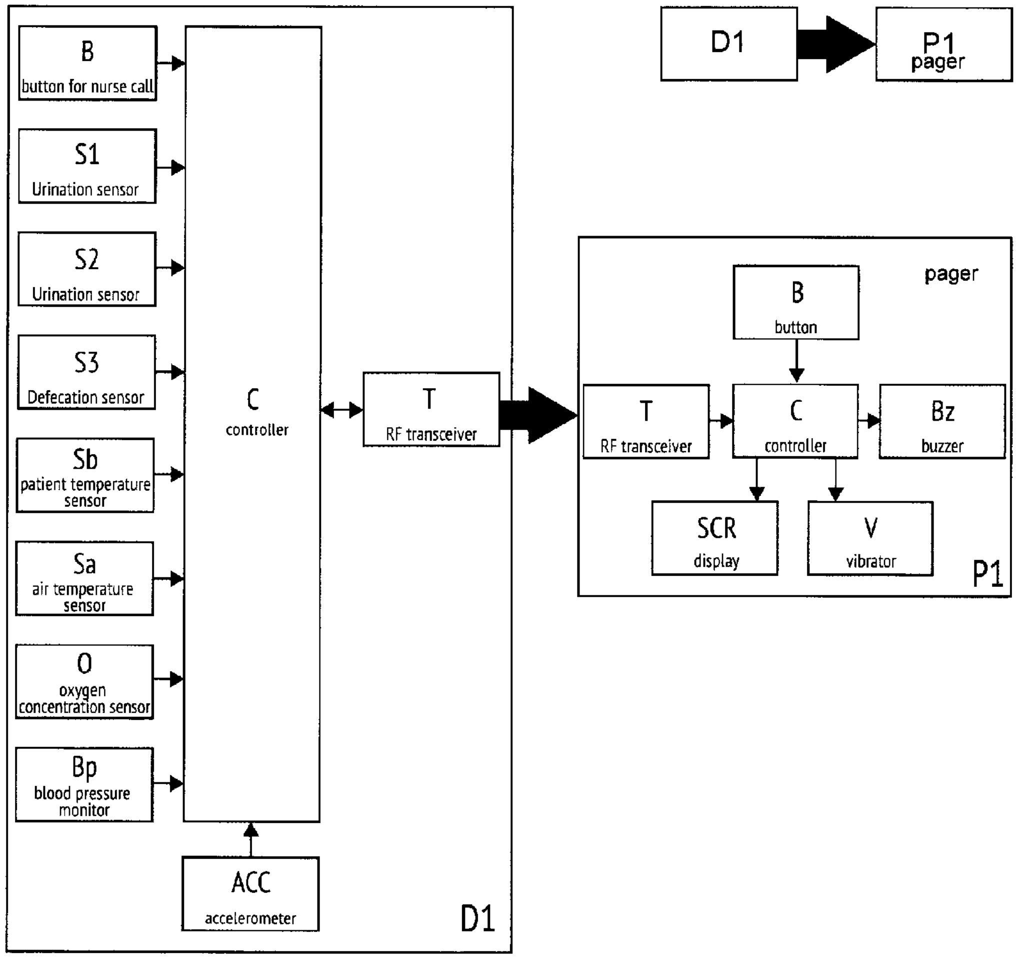
FIG. 1 is a schematic diagram and circuit diagram illustrating a monitoring system according to a first embodiment of the invention.

With reference to FIG. 1, a first embodiment comprises a system for monitoring patients in nursing homes, hospitals or home care where a patient has a multi-sensory device D1 which wirelessly communicates with one nurse pager P1 such as by radio frequency signals. Preferably the devices D1 have a long RF range of a minimum 100 yards, transmitting for example at 900 MHz. As shown in the schematic circuit diagrams of FIG. 1, multi-sensory device D1 incorporates urination sensors S1, S2, defecation sensor S3, body temperature sensor Sb, air temperature sensor Sa, reflective pulse oximeter O, blood pressure meter and pulse detector Bp, accelerometer ACC, micro controller C, and RF transmitter or transceiver T. Micro controller C may be for example a PIC micro controller from Microchip. Accelerometer ACC may be for example a Freestyle Semiconductor's micro-machined (MMA) series accelerometer. Accelerometer ACC outputs are wired to microcontroller C analog to digital inputs. A nurse call button B may be provided on D1.

Nurse pager P1 may have a display SCR such as an LCD color display, cell phone vibrator V, buzzer or beeper Bz, micro controller C, and RF transmitter or transceiver T. Button B on P1 may be provided to be pressed after an alarm is resolved, which will cancel the alarm on P1 and the alarm display on SCR.

Figure 2:
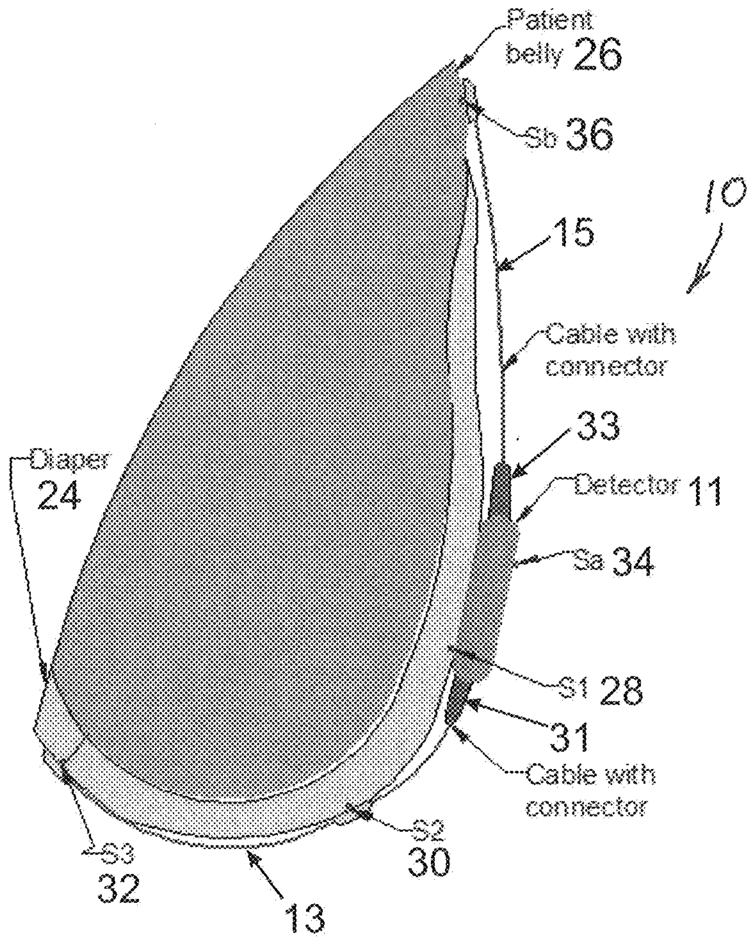
FIG. 2 is a cross-sectional view illustrating the multisensory device installed on a diaper.

With reference to FIG. 2, a first embodiment of multisensory device D1, designated as 10, is illustrated attached by adhesive tape to a diaper 24 worn on patient 26, shown in cross-section. Urination sensors 28 and 30 and defecation sensor 32 are attached to the outer surface of diaper 24. Body temperature sensor 36 is attached to the skin of patient 26. Air temperature sensor 34 is provided on the exterior of device 10. Oximeter O and pulse and blood pressure sensors Bp can be together in the same sensor body with temperature sensor 36 and connected through the same jack connector to detector body 11 or can be separately connected to detector body 11 through a cable as other sensors. Oximeter O and pulse and blood pressure sensors Bp can be applied directly to the patient body, for example on a finger, stomach or on a leg.

Figure 3:
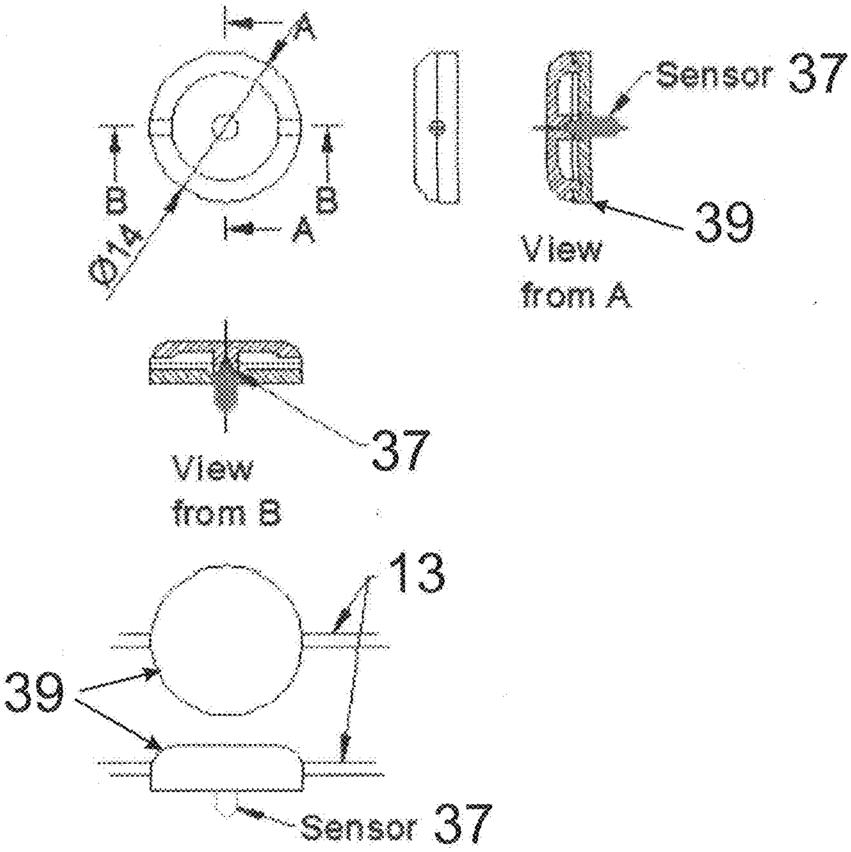
FIG. 3 illustrates the construction of a temperature sensor according to the invention.

With reference to FIG. 3, urination sensors 28 and 30 and defecation sensor 32 are preferably temperature sensors which may each comprise thermistors 37 of the type used in electronic medical thermometers, stainless steel covered, which are each fixed in and extend from a plastic disc as shown in FIG. 3. Urination sensors 28 and 30 and defecation sensor 32 may for example be secured to the diaper 24 exterior surface by a removable adhesive surface attached to the sensor. Preferably two sensors are used for sensing a urine event and one for defecation. For infants a single urine sensor may be sufficient. As illustrated, one urine sensor 28 is on the detector body 11 which is a plastic shell in tight contact with the diaper 24 and the second sensor 30 is on the cable 13 as described. For better sensitivity there can be more than two sensors for urine and more than one sensor for defecation events, all located at appropriate locations on the surface of diaper 24. Sensors 37 have a stainless steel cover and are soldered/assembled on a thin elastic printed circuit board (PCB) film. This film is covered with an elastic insulator. Only the tip of sensors extend from this elastic plastic cover so they can be in tight contact with diaper 24 to ensure a sensitive measurement. Numerous sensors on all surfaces are not required since the wetness spreads in the absorbent material in the diaper, to which the diaper exterior surface is tightly connected, so temperature change is conducted over a large surface area.

Figure 5:
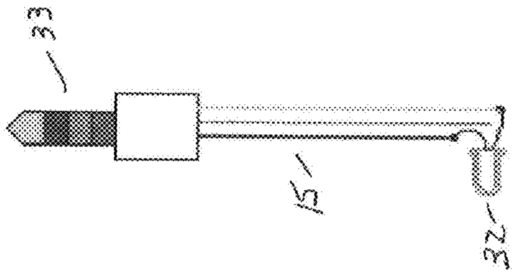
FIGS. 4 and 5 illustrate two variants of the sensor connections shown in FIG. 2.
Figure 4:
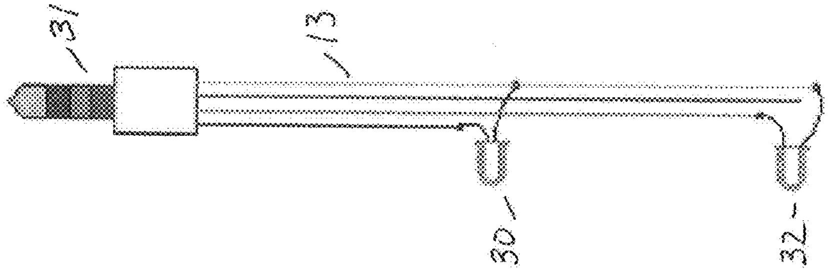

As shown in FIG. 4, both urine sensor 30 and defecation sensor 32 may be connected to the device through a single cable 13 and jack 31. Jack 33 and cable 15 as shown in FIG. 5 connect a single sensor and can be used to connect body temperature sensor 36 when connected to the upper side of detector body 11 or the defecation sensor 32, when it is connected to lower side of detector body 11. Either jack 33 with one sensor or jack 31 with two sensors can be connected to the lower female connector depending on the size of the patient, smaller for jack 33 and bigger for jack 31, and the software on microcontroller C distinguishes which sensors are connected to each female connector. Jacks 31 and 33 can be of the audio plug type and cables 13, 15 are preferably flexible cables less than 1.5 mm in diameter.

Device 10 measures outputs from the accelerometer ACC and all other sensors, preferably very frequently, for example, at least 10 times per second. Accelerometer ACC measures co-ordinate acceleration and also orientation and can measure position by reference to a fixed position, whether pre-defined or taken from a GPS, through measurement of the change in co-ordinate motion. The ACC integrated circuit is positioned on device 10's printed circuit board (PCB) in such way that its sides, the PCB sides and detector body 11 plastic shell's sides are aligned. ACC position or orientation is the same as patient position or orientation and thus patient position or orientation is determined by measuring and interpreting the ACC three axis outputs. This also applies when the ACC measures acceleration. Acceleration and position or orientation is given by those three axes' amplitude. Adding those three outputs provides patient motion intensity. By interpreting each of the three outputs' amplitudes/values, the patient walking/running direction, steps cadence and speed can be calculated. Such measuring at high frequency, such as at least 10 times per second, is necessary to determine when the patient leaves his/her bed or when the patient urinates or defecates.

Incontinence Detection

For incontinence detection and measurement, generally urine or feces are a few degrees warmer than the temperature measured on the diaper 24 exterior surface. Sensors 28, 30, 32 measure temperature on the diaper surface. When urination or a bowel movement occurs there is an increase of temperature of 0.5 to 2 degrees Celsius at the diaper surface 24. Urination or feces liquids are immediately absorbed in the diaper and that leads to an increase of diaper surface temperature. This sudden increase is interpreted by microcontroller C in D1 as a urination or bowel movement. Microcontroller C may measure the variations of temperature continually or only if there is a minimum variation within a certain period. The difference between urination and defecation is detected by the position of the temperature sensor where the temperature increase occurred. For example if in a certain period of time there is measured at one of the sensors 28, 30 or 32 a temperature rise of a certain minimal value such as 0.2 degrees, this rise is interpreted by controller C as a urination or defecation detection, depending on which sensor was detected. The specific temperature rise will depend on the specific type of diaper, whether paper or cloth, size and thickness of the absorbent material, diaper starting temperature, and urine or defecation quantity and rate of flow. While infant diapers do not differ significantly in thickness of the absorbent material from adult diapers the surface area of adult diapers is considerably greater but for both types of diaper the wetness travels quickly to the diaper surface for detection by the sensors 37. The temperature rise will also depend on the frequency of incontinence events. A greater frequency of events will mean less time between each event and less temperature rise at each event, but no matter how high the frequency is there will always be a minimal rise, for example of at least 0.2 degrees detected within a certain time period. The increase in temperature at the diaper outer surface can also be influenced by the patient's position or orientation in bed. For example if and when a patient turns face down, the multi-sensory device 10 comes between the patient and the bed which further insulates the diaper and temperature measured at the diaper surface can increase a few tenths of a degree. In this case the microcontroller C will take the position or orientation measured by the accelerometer ACC into the calculation in determining whether an incontinence event has occurred. The temperature at the diaper surface can also be affected by the patient uncovering herself and by a change in the ambient air temperature, which the microcontroller C will take into account from measurements at sensor 34.

Figure 14:
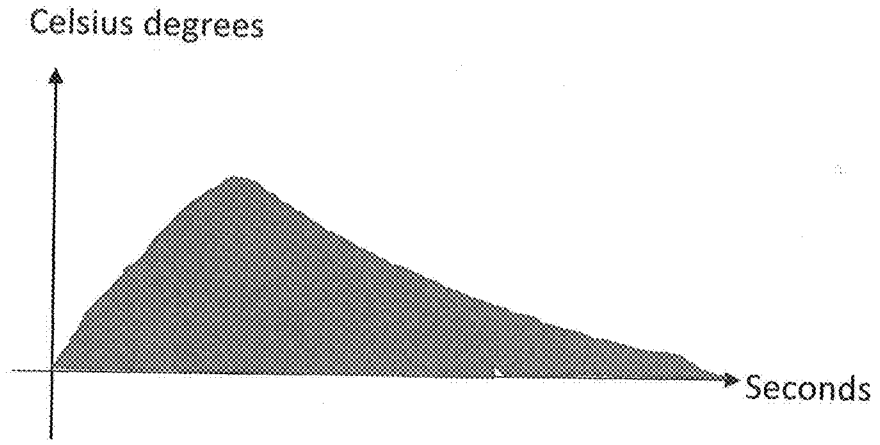
FIG. 14 is a graph illustrating detection of events by a temperature sensor.

When an incontinence event occurs the temperature at the diaper surface varies with time. The graph of temperature as a function of time (FIG. 14) is interpreted by microcontroller C. The rate of temperature rise depends on velocity and volume of flow of the urine or feces and temperature of the urine or feces. With some corrections from empirical data, microcontroller C can calculate with approximation the maximum flow during the urination or defecation and the total quantity of urination or defecation. With reference to FIG. 14, the size of the area under the graph is a function of the volume of waste material or liquid which is calibrated empirically. Any small sudden increase of temperature within seconds at the diaper surface signifies that a urination or defecation has occurred no matter how small the quantity is. Microcontroller C takes into account the starting temperature, rate of increase, time to the maximum temperature, and total temperature rise, as well as the patient position or orientation and temperature at sensor Sa, 34, to estimate volume and rate of flow of each event. Microcontroller C calculates and records the measurements and determines when an alarm condition is fulfilled. When the maximum number of urinations or defecations is reached, an alarm can be signaled and sent to pager P1, or whether these detections occurred too often or they were too rare. These may be symptoms of patient problems such as diarrhea, constipation, cystitis, prostate problems, etc. When a urination or bowel movement occurs the pager P1 receives the detection signal and displays that there is a urination or a bowel movement. The pager also counts how many times these events occurred.

One of the advantages of this method is that the system can detect more than one urination or defecation in the same diaper with reusable sensors, which work outside on the diaper surface. That is of benefit for the patient as well as for nurse and health care facility by savings on diapers and nurse time.

Figure 6:
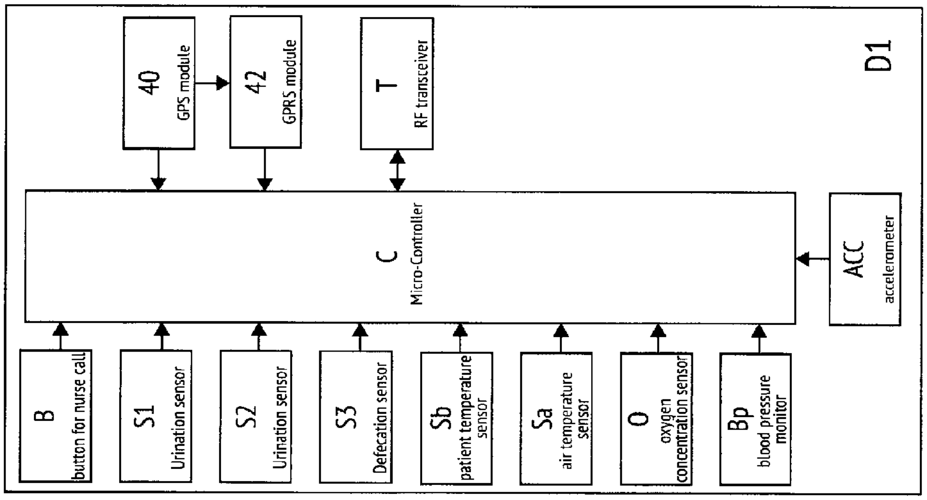

A Multi-Sensory OFF alarm is given when the multisensory device 10 falls off of the patient diaper or skin. This detection is done with heat sensor 28 located on detector body 11 and in direct contact with diaper 24. When Multisensory device 10 is off of the diaper, controller C measures a decrease in temperature at this sensor 28 and gives the alarm. Sensor 30 OFF and/or sensor 32 OFF alarm is achieved in the same way. When C measures a decrease in temperature at one or both of these sensors this alarm is given. In a situation where only one sensor 32 is connected to multisensory device 10, an alarm is given correspondingly. These alarms may be given by sound and visually whether on computer and nurse pager P1 and are recorded in the computer. When at least one of the above alarms are given, multisensory device 10 may not transmit any data until the nurse reattaches the parts and pushes the reset button Another embodiment of multisensory device 10, shown as D1.*a* in FIG. 6 contains all or some of the sensors as shown in the embodiment in FIG. 1 plus an extra GPS (Global Positioning System) module 40 and a GPRS (General Packet Radio Service) module 42 in the same device. Device D1.*a* communicates with pager P1 as shown in FIG. 1 by 900 MHz radio-frequency signal. When the patient associated with device D1.*a* exceeds a prescribed distance from the facility or comes out of RF range, microcontroller C turns off transmitter or transceiver T and turns on the GPS module 40 and GPRS module 42 and transmits periodically messages containing patient coordinates to a nurse/caregiver pager P1 or smart phone (see smartphone 118 as described in FIG. 11 below). A specially designed application in the nurse's pager Pi or smart phone allows the nurse to see the patient's position on a map. A multisensory device 10 having the features of D1.*a* can be used in the other two embodiments D2.*a* and D3.*a* described below.

Figure 7:
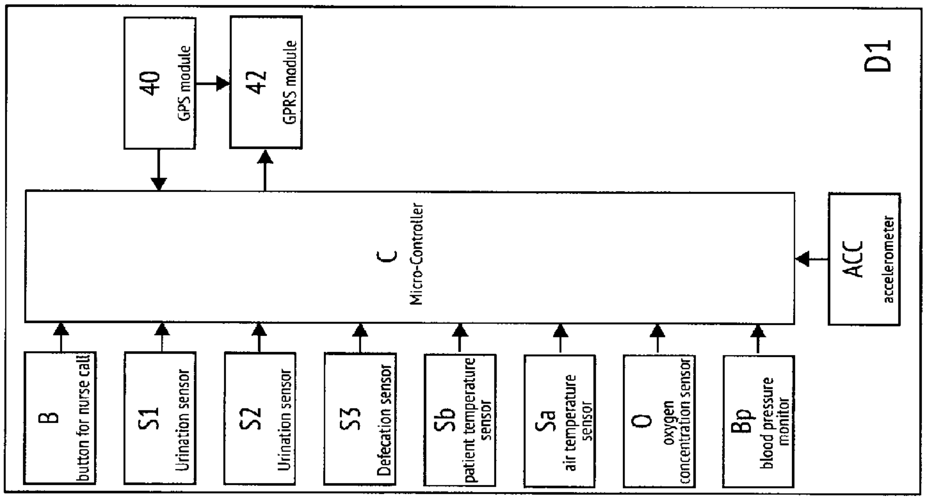
FIG. 6-8 are schematic diagrams illustrating the circuitry of alternative embodiments of the multisensory device.

FIG. 7 illustrates another embodiment of multisensory device 10 designated D1.*b* similar to D1.*a* but without a transmitter or transceiver T. Alarms and data are transmitted by GPRS as coded SMS messages to a nurse/caregiver pager P1 or smart phone. A custom application in the smart phone decodes alarms and data and displays it by sound and on screen. All data is recorded in smart phone memory to be downloaded later. In a healthcare institution or even in home care, a smart phone may send all data received to a server by Wi-Fi. Alarms can be received at any distance between patient and nurse. A nurse smart phone can receive alarms and data from more than one patient each having a device 10 as in D1.*b*. When the caregiver/attendant activates from his/her smart phone the GPS module in D1.*b*, patient position can be detected with nurse smart phone as in D1.*a*.

Figure 8:
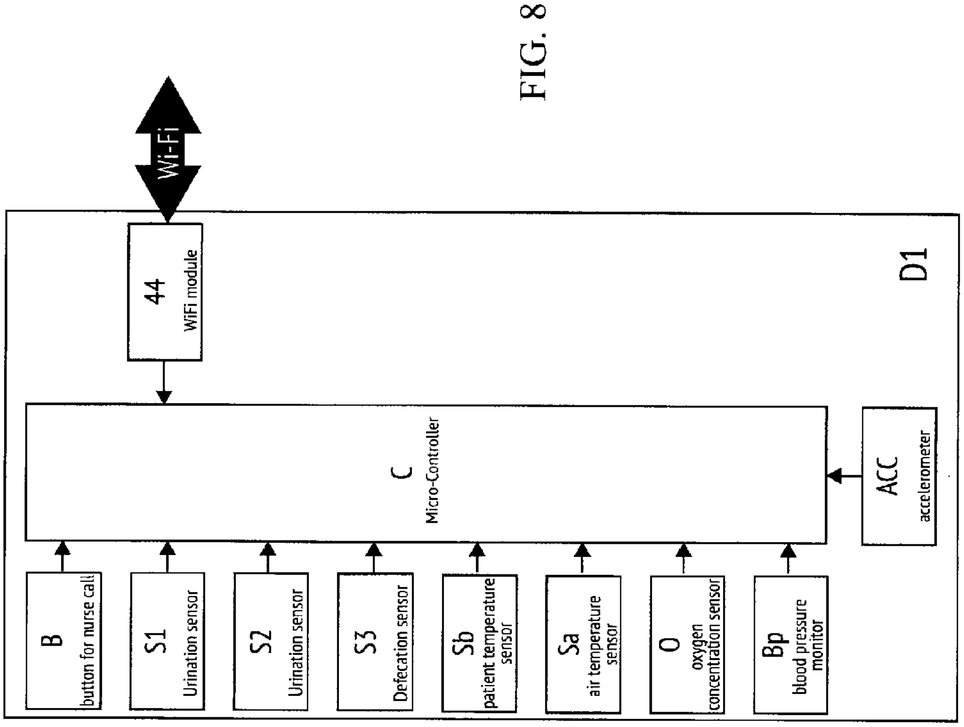

FIG. 8 illustrates another embodiment of multi-sensory device 10 designated D1.*c* and contains all or some sensors as in the embodiment shown in FIG. 1 plus a module 44. It transmits alarms and data through the facility's Wi-Fi to a server and nurse pager P1. D1.*c* can communicate data with the patient's smart phone or issued pager (not shown), which transmits data further to a server. Device D1.*c* sleeps when there is no alarm to be transmitted and wakes up just to transmit the alarm. In a homecare version D1.*c* communicates directly with a smart phone which displays and records data in it. It can be any smart phone having installed the required application. The advantage is that the attendant's own smart phone can be used for this purpose. Alarms can be received anywhere a Wi-Fi service is available in the facility. D1.*c* can also be used in the embodiments shown In FIGS. 1, 6 and 7.

Fall and Wandering Alarms and Pressure Ulcer/Wound Management Detection (Turn-Check)

Fall and Wandering prevention and alarms are possible due to the accelerometer ACC inside multisensory device 10. ACC through C detects patient position or orientation at any time. C measures at its analog to digital inputs all three ACC outputs and by them calculates patient position or orientation. Device 10 is affixed upside up on the patient's front, on the diaper as in FIG. 2 or on the patient's body front, with adhesive tape. The position of the accelerometer ACC and its three outputs depends on device 10's position. Being affixed on the diaper 24, the accelerometer ACC output thus depends on the diaper wearer position or orientation. Microcontroller C in device 10 measures ACC outputs and calculates patient position or orientation by its software. All position or orientations such as Stand Up, Lay Down, Left Side, Right Side, Face Down, Face Lip are transmitted to nurse pager P1 or server and monitoring application MA through interface 12, 14 and Wi-Fi as described below in the second and third embodiments. MA analyzes these position or orientations and their timing and sends alarms and data by Wi-Fi to pager P1.

OFF SEAT alarm is used in situations where it is important to get an alarm when a patient just rises from a seated position. In that case device 10 is affixed on the patient's thigh front so that device 10 is upside up when the patient is standing. The alarm may be off when patient half rises and an alarm, which may include a local beeper or vibrator included in Detector 10 to alert when the patient rises out of a chair. To record patient motion, ACC outputs for patient movement and acceleration are measured by C in multisensory device 10. In this way patient movement and steps can be detected. Knowing the timing between steps, number of steps and the acceleration of each step, C can calculate the speed, distance walked or run by the patient, motion intensity and total motion in a certain time, like a nurse's shift or a day. A patient agitation alarm may be given when a prescribed motion acceleration value stored in the MA table is reached or exceeded. Values of motion as a result of ACC output values are determined based on empirical data. In order to determine patient motion intensity per unit of time, C receives accumulated measurements from all three outputs of the ACC over a short period of time, on the order of a few seconds.

A Patient Fall is detected when the patient changes his/her position from Stand Up to Lay Down in less than a certain time and a certain minimum motion has been detected. The parameters for analyzing this data is determined empirically. An Up and Go alarm is detected when patient changes position from Lay Down to Stand Up in less than certain time and immediately thereafter walks a few steps. Walking is calculated from motion intensity and variation of acceleration on a certain axis which shows when the patient made each step. If this alarm is associated with distance between D2 and I2 (defined below) it shows with certainty when patient left his/her bed. The ACC can identify patient lying face up, face down, left or right side, and stand up, and alerts the nurse when patient is agitated, and moves too quickly. It further alerts nurse when patient has left bed and taken steps. The MA can program patient's maximum range of travel, in association with the GPS can locate the patient inside or outside the facility radius, and the nurse sees patient location on her pager screen.

UP alarm is given when patient position or orientation has changed from Lay Down to Stand up in less than a certain time limit. Position alarm is given when patient is in one of the selected positions listed in FIG. 19. The Wound Management or Turn-Check alarm uses the same ACC whose outputs are analyzed by C and transmits patient position or orientation to MA through I2 or I3, Wi-Fi and server S2 or S3. In this case only position or orientations in bed are needed, such as Left Side, Right Side, Face Down and Face Up. MA analyzes the time patient was in one of these position or orientations and if the patient did not turn to another position or orientation within a prescribed time tries first to wake the patient by waking sounds by MP3 module. If the patient does not wake up, for example, after 15 minutes an alarm is sent to nurse pager P2 or P3 such as through a server and the MA. A minimum time and a maximum time can be set in the MA table (see FIG. 19). Both are as set, for example by a doctor. The minimum time, also called Oxygenation time, is the minimum for a certain position or orientation to be considered as enough for oxygenation of a wound. If patient stays less than this time in a position or orientation, the system does not consider that the time was enough for re-oxygenation of body wound. Usually this time is around 15 minutes. If the patient stays in one position or orientation longer than the maximum time prescribed and entered in the MA table, at first wake-up sounds are played to the patient, then the alarm of Turn-Check is sent to nurse pager P2 or P3.

Thus the three axis accelerometer ACC sends its data on three lines to its amplifier and its microcontroller C. Each line corresponds to variation in accelerations on one of the three axes. The position of the accelerometer ACC is given by the Detector D1's printed circuit board contained inside of the Detector D1. Slight breathing motion may also be detected with the accelerometer ACC. Different position or orientations of diaper wearer are detected with accelerometer ACC. If no motion has been detected a no motion alarm is sent to pager P1, P2 or P3. The table in the MA in FIG. 19 can be set to send an alarm when the patient comes out from a coma or from a very long period of no motion. All data from accelerometer ACC are transmitted, received and displayed in real time.

Breath detection is obtained with the same accelerometer ACC by adding an amplifier to the 3 outputs of the accelerometer and programming it accordingly in Controller C. Controller C measures and calculates all outputs from accelerometer ACC. Breath count and its frequency is done by measuring and interpreting ACC outputs oscillations in time, their maximums and minimums and counting them. If in a certain time period these outputs are under a certain value determined by preliminary tests, absence of breath or motion has been detected and an alarm is sent to pager P1. If a patient stops moving and breathing an alarm is signaled and a Nurse can intervene. This detection may saves lives in newborns' Sudden Death Syndrome (SID) and patients of all ages whom breathing have stopped or their motion decreases almost to zero. Also it is useful for patients coming out from coma and start moving. In this case monitoring table MA is setup to alarm when patient starts moving.

Figure 15:
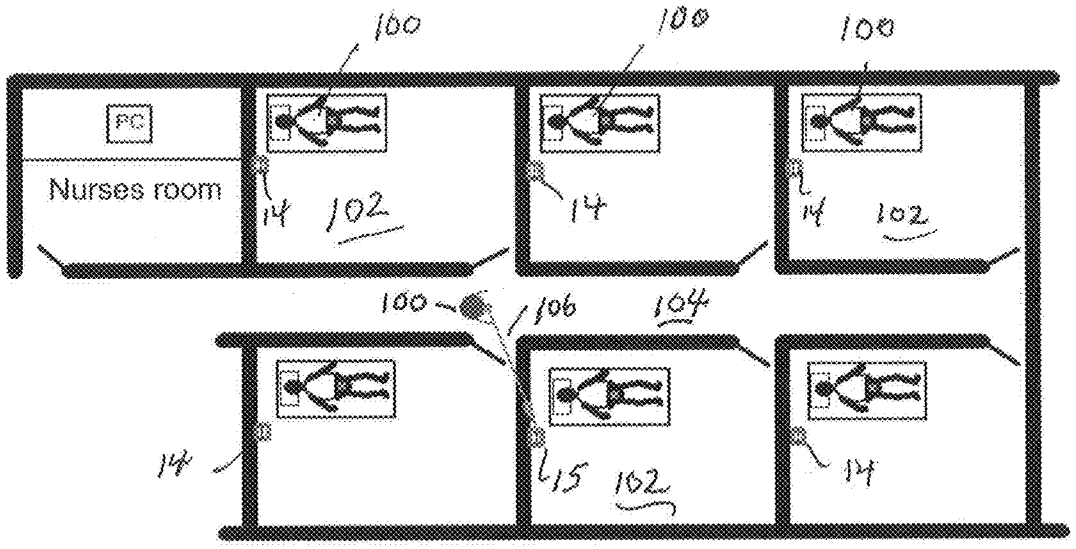
FIG. 15 is a schematic diagram illustrating the functioning of the invention in a multi-room healthcare facility.

Patient wandering and location detection in an institution is detected as follows. FIG. 15 is a schematic of a section of an institution in which each patient 100 has his/her own multisensory device 10/D1 on his/her body on a diaper or secured to the patients's body with adhesive tape. Patient position in a room 102 can be in bed or out of bed. In each room 102 a patient interface 14 is provided. Such interfaces are at fixed locations with power supplied through wall outlets. In the hallway 104 is a patient 100 who may be walking. All interfaces in the vicinity receive the transmission from the detector D the patient. Each reception has a certain amplitude, which depends on the distance to D. Interface 14 measures this amplitude and sends it to server S2 together with D's and I's identification code. Server S2 considers the greatest amplitude which corresponds to the closest interface 15. The identification code of the closest interface 15 is displayed on the server monitoring application and on the nurse's pager for each detector. In this way the location of each patient is always known. Patient location detection is handled the same in the second and third embodiments.

Figure 9:
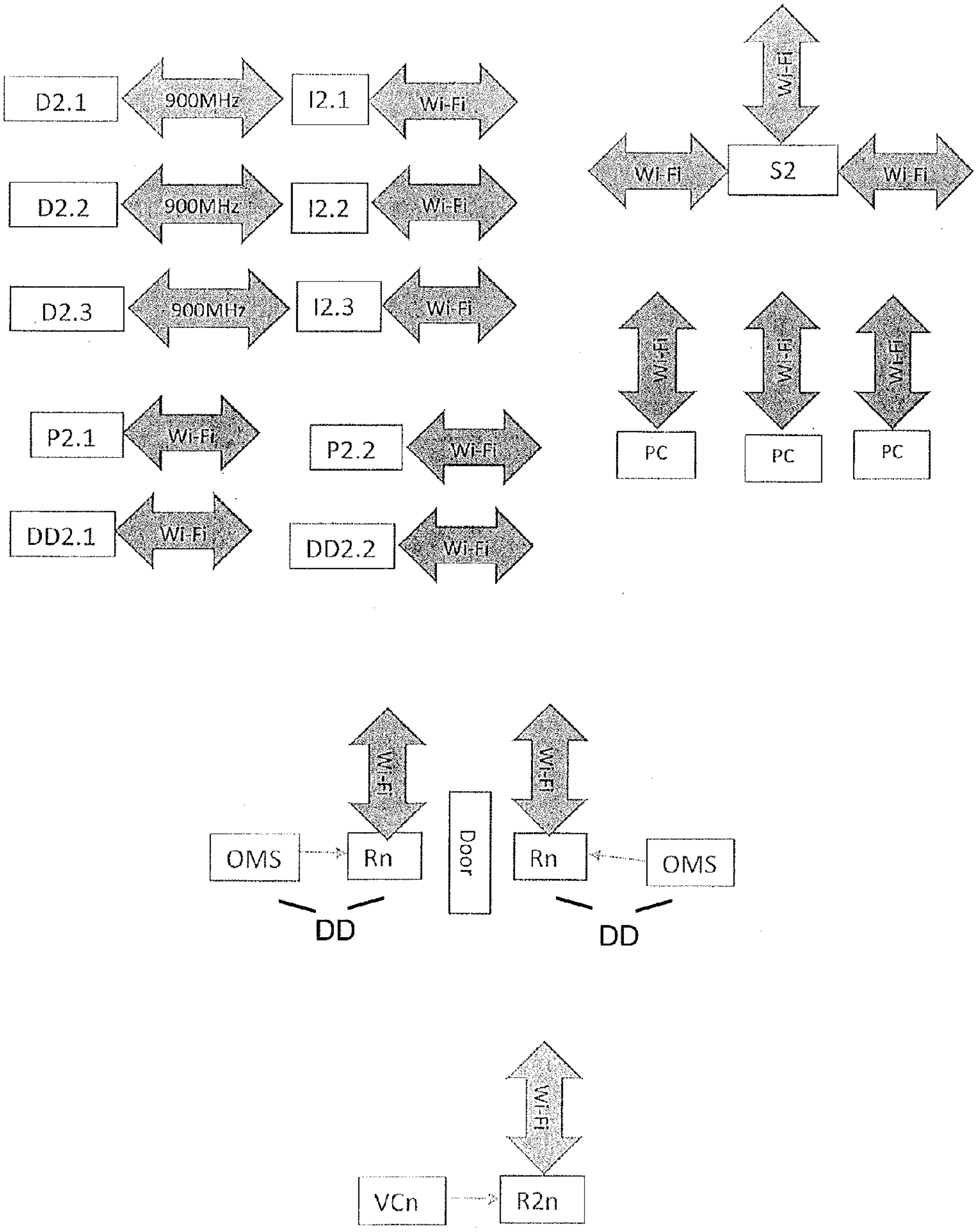
FIG. 9 is a schematic diagram illustrating an embodiment of the communication system used in the invention.

In order to improve patient location detection accuracy, a multitude of door detectors DD as in FIG. 9 can be installed on doors. Door detectors associated with described location detection method can give a better idea about patient location, the door he/she is at and the direction patient has passed door. Such door detectors can be installed at all doors or only at main doors such as entrance or back doors which go outside. These repeaters Rn are wall plugged for power with voltage adapters and are on all the time. A door Detector DD comprises one repeater R connected to an optical motion sensor OMS installed on top of each side of the door. Optical sensors are oriented in such a way to detect patient only when is very close to the door. When patient approaches the door on one side, optical motion sensor detects patient and wakes R up. Repeater R "interrogates" patient Device 10 and finds out its identity. If there is more than one D close to the door R considers only the one with stronger reception and closest. Then when the patient passes the door, motion sensor on the other side of door detects the patient, wakes the repeaters Rn up and interrogates the D finding out its identity. If the identity is the same as Detector's identified before, the RF signal is most powerful and this signal decreases as the patient moves away from the door, R sends data to PC about which patient passed that door and what was his/her passing direction. In this way door detector DD detects through which door patient passed and what direction patient had. If that door detection is activated in MA, the server sends an alarm to pager P2 or P3. DD functions are patient sensing and identifying, location detection and direction of passing. Video camera VCn is located over the patient bed or in any other places of interest. It is wired to a repeater R which is an interface I2 or I3 without MP3 module. Repeater transmits video or still images to server 52. VCn are wall plugged for power with voltage adapters and are on all the time. Images are seen on the computer PC and nurse pager or tablet.

Transmission frequency varies as function of patient position, mobility and location. When a patient is in bed, transmission frequency is low, perhaps once in 10-15 minutes in order to not expose patient too much to Rh radiation. Meanwhile any alarm can go off if necessary. Or, when patient has left the bed, transmission frequency increases for more accurate location of the patient. Nurse Call is produced when button B is pressed on device 10 and if this alarm is checked in the monitoring application MA table 200 in server S2 or S3. Nurse Reminder is an alarm to remind nurse when she has to do something. It produces an alarm if alarm is checked in MA table 200. The reminder allows the nurse to enter the specified time of reminder and what the nurse has to be reminded about.

A Distance alarm is given when a certain value in MA table 200 or location is reached and only if this alarm is checked in the table. Values are chosen conventionally and are approximately proportional to the distance between device 10 and interface I2 or I3. They are obtained by measuring the amplitude of signal received by transmitter, transceiver T in I2 or I3. The location is determined as the closest interface.

Too Hot and Too Cold alarms are generated as a function of the values written in MA table 200 at Air Temp cold and hot temperature limits. If the measured temperature by sensor 34 is equal to or less than the limit prescribed at Cold column in the table 200, a Too Cold Alarm is generated. If the measured temperature is equal to or higher than the value recorded at Hot column in MA table 200 a Too Hot alarm is generated at pager P1 or 118 (P2 or P3). Ambient air temperature is always displayed at pager P1 or 118 (P2). A Fever alarm is generated if temperature measured at sensor 36 is equal or bigger than value recorded in table under Body Temp (see FIG. 19). Thus Sensor 34 sends to microcontroller C data about temperature at the detector 10 exterior surface. If the diaper wearer is uncovered or it is too cold or too hot, the pager 118 alarms the attendant. Alarms are also given if measured pulse, oxygen concentration in blood and blood pressure are out of setup limits. Air temperature and body temperature are measured at all times for all patient locations to protect the patient's life.

Data transmission from D1 device 10, occurs at equal intervals of time and is organized in bits of data which are transmitted sequentially as binary strings. In this binary string each bit relates to a certain detection and the order of it is strictly the same in each transmission. Such binary string contains in sequential order: a code of identification of device 10 followed by 0 or 1 if device 10 works in normal mode with occasional (10 minutes) sync transmissions or in search mode (once or twice per second), urination detection (0 or 1), defecation detection (0 or 1), urination event quantity in a certain # of bits, defecation event quantity, urine maximum flow, 6 bits showing six position or orientations of up, right side, left side, face up, face down, lay down, nurse call (0 or 1), a certain number of bits expressing body temperature, a certain number of bits expressing the air temperature, a certain number of bits expressing motion intensity, low battery alarm, alarm off chair, Stand Up alarm, Fall alarm, Agitation alarm, UP & Go alarm, Lay Down alarm, oxygen concentration, blood pressure and pulse. The distance between device 10 and pager P1 or interfaces I2, I3 as described below is calculated in the pager or interface as a function of reception strength.

A second embodiment illustrated in FIG. 9 has one or a multitude n of multi-sensory devices D2.*n* each having the features of device 10 as described above. There are one or a multitude of interfaces I2.*n*. Server S2 may be one or a multitude of local computers and individual computers PC communicate over the internet by Wi-Fi with interfaces I2.*n* and pagers P2.*n*. One or a multitude of Nurse Pagers (shown as P2.*n*) is also provided. Devices 10 shown as D2.1, D2.2 etc. have the same construction and functions as device 10 in the previous embodiment. Incontinence, Fall and wandering alarms and Wound management detection and/or measure can be provided in all the described embodiments.

Figure 10:
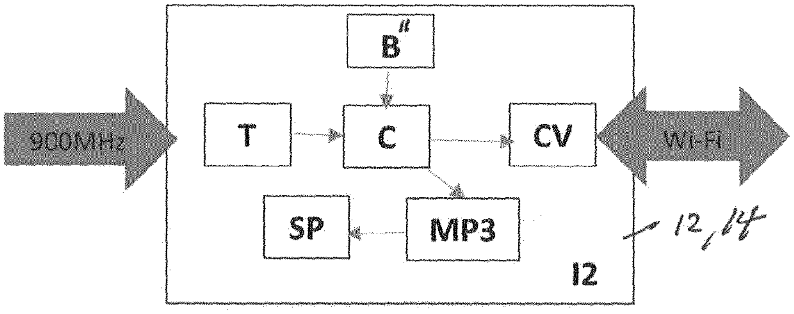
FIG. 10 is a schematic diagram illustrating an embodiment of the patient interface used in the invention.

With reference to FIG. 10, interface I2, shown as 12, 14, is located always next to patient bed. It comprises a receiver or a transceiver T and microcontroller C. CV module is a converter. It converts signals from microcontroller C into Wi-Fi and sends them to server S2. MP3 is an MP3 module controllable by microcontroller C. SP is a speaker. B is a button on I2. A nurse presses this button after she resolves an alarm. The monitoring application (MA) understands that the alarm has been resolved and stops flashing red the alarm on computer PC screen and on pager P2.

In this further embodiment interface 12, 14 (I2) may contain an extra phone module GPRS which sends data to pagers P2 which are smart phones or to computers PC. In this variant, as in D1.*a* and D1.*b* a GPRS module receives data from D and serves as safety backup in case Wi-Fi does not work. In a further embodiment of I2 the module GPRS may replace the Wi-Fi module. In this situation in which there is only GPRS module and no Wi-Fi module the system can be used in places where is no Wi-Fi.

In the first embodiment, transmissions from D1 to P1 are synchronized with crystals of high accuracy. These crystals are electronic components used to sync two devices. In this way P1 turns its reception on exactly when a transmission from d1 is expected. This is necessary to save battery life in P1 and because frequency of transmission varies as a function of patient position and motion. Transmissions are rare when a patient is in bed or in a room and are more frequent when the patient stands up and/or is moving. This is detected when Stand Up, Up & Go and distance alarms are triggered. Resynchronization is necessary for the first embodiment shown in FIG. 1 and is done when device 10 and pager P1 are restarting or when synchronization is lost due to RF range overpass. In case transmitter T in device 10 and pager P1 is a transceiver both devices 10 and pager Pi know their transmissions have not been received because device 10 does not receive back reception confirmation. In case T is a transmitter, pager P1 knows when transmission is lost if they do not receive a transmission within a certain time. Making sure the alarm of Sync is off, Resync is done as follows: device 10 continues its transmissions. Pager P1 turns on its receiver for a time which is longer than the sync interval and synchronizes its reception at the moment of receiving two consecutive transmissions from device 10. The interval between two synchronization transmissions can be for example between 1 second and 10 minutes. Alarm transmissions are done immediately when they are detected. Pager P1 reception is on each second and it turns on for a period of time 5% longer than the time of a whole transmission, to cover time error from device 10. For purposes of a perfect synchronization, each time pager P1 receives it readjusts its reception timing after the last reception. If device 10 and pager P1 both have transceivers instead of Transmitter and Receiver it is advantageous for an easier synchronization and safer data reception, but power consumption at device 10 and pager P1 is increased. The advantage with using a transceiver is that pager or interface transceiver respond to device 10 transceiver to repeat transmission if data reception is not accurately received. This is important especially for alarms transmission accuracy and for patient identification. In case of a transmitter at device 10 and a receiver at pager P1 each alarm is transmitted three times in order to be sure it was received and identification is done correctly. In the second and third embodiments, interfaces I2 and I3 do not need synchronization with device 10 because they are on continuously, being supplied with power from a wall plug.

Microcontroller C in pager P1 or interface 12, 14 receives data from device 10 through receiver or transceiver T and compares number of bits and binary string structure to the model it has in its memory. If they do not correspond that transmission is not considered as good and it is not considered at all. If they correspond microcontroller C further reads the identification code from its memory. If it finds it to be correct, microcontroller C considers the transmission as good and reads the detections in the data string. If the ID code is not the one pager P1 has it in its memory the reception is canceled. In the case of homecare where usually there is only one device 10 and pager P1 this does not occur. If there are multiple patient devices then this identification is useful.

Minimizing power consumption of device 10 is necessary. All companies making RF components try to minimize their products' power consumption. This is important for device 10 and its battery to be as small as possible and to last as long as possible. This can be achieved by optimizing the frequency, power and duration of transmissions. In a case where the patient is in bed, as detected by his/her Lay Down position and by the small distance between the device 10 and P1, device 10 transmissions are made only when an alarm is detected or when patient location detection is needed. In case of device 10, in addition to alarms or data transmissions there are also transmissions for synchronization. Synchronization transmissions are rare (e.g. every 10 minutes). When a patient has left the bed, communication turns from normal mode to search mode and as a result transmission interval is much decreased. While the patient is in bed in position Lay Down or no motion is received from ACC, or the patient is close to pager P1 or to the patient interface, transmission power is reduced/optimized on the closest pager/interface reception and the interval between transmissions is reduced dramatically. While in search mode transmission frequency is decided inside D1 depending on the patient motion. Greater motion leads to greater frequency. Optimizing power of transmissions is another way of saving power in D's battery. This is only possible with T as a transceiver in device 10 and pager P1 and it works as follows: when a signal received by the pager/interface is greater than a certain minimum amplitude prescribed in its software, the transceiver in the pager/interface 'tells' the transceiver T in device 10 to reduce correspondingly its transmission power. With these optimizations in transmission frequency and power it becomes possible that D can work with a coin battery such as CR2032 for a long period of time. In the case of device 10, a GPS and GPRS module's power consumption is significantly higher and they can be used only a short time and only in case of emergency. In case of the embodiments in FIGS. 6 and 7, the GPS, Wi-Fi and GPRS modules need a bigger battery.

Being worn on patient body, device 10 needs to be as small as possible. The patient can be an infant, a pet or a senior. This device size minimization is done by choosing a non-rechargeable small lithium battery which lasts a minimum one week or a built in lithium rechargeable battery. Optimization of battery consumption applies in the same way as above for the second and third embodiments.

Regarding pager P1 features, pager/smartphone P1 may contain any or all of the main features: incontinence, Fall and wandering, Turn-Check, Oxygen concentration detection, Blood pressure and Pulse meter. When an alarm comes up it is displayed on pager P1 screen and/or by sound or vibration. Prescribed values or settings of all alarm limits are recorded in pager P1 menu in a similar but simpler manner as they are recorded in the embodiments 2 and 3 described below which have a monitoring application MA table (see FIG. 19) in the system computer. PI may contain all features but only the feature that has been paid for is activated. If a customer wants more features activated he/she goes to company website, pays for more features and receives a software update which if installed in Pager PI activates the features he/she paid for. This same feature applies for embodiments 2 and 3. In embodiments 2 and 3 activation of new features in the system after payment was received is done automatically over the connection to the internet. The fact that multiple functions can be provided with limited hardware and software thus creates the possibility of making the same products with more or less activated functions. These individual functions can be separately activated for a certain period of time and activated or deactivated even online, using the same hardware.

Figure 11:
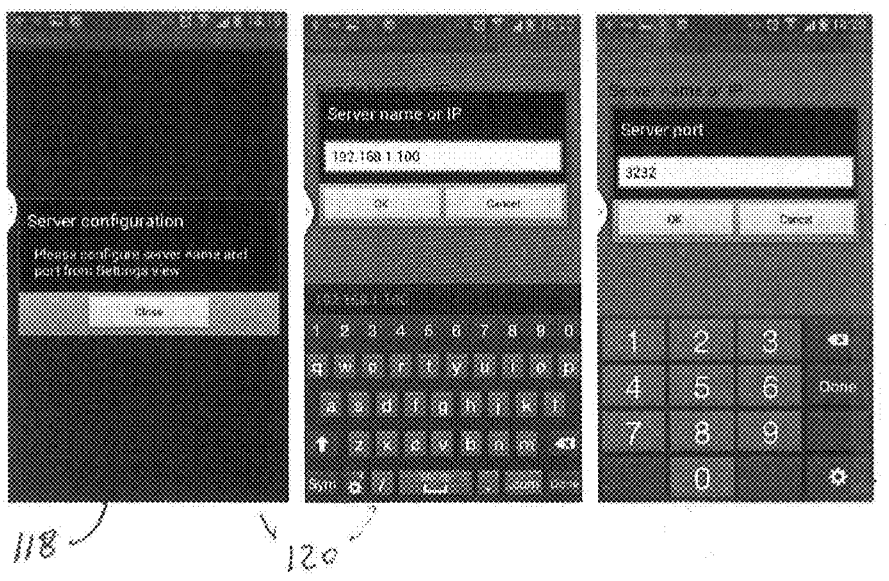
FIGS. 11 and 12 are screen shots of a caregiver smartphone used in the invention.
Figure 12:
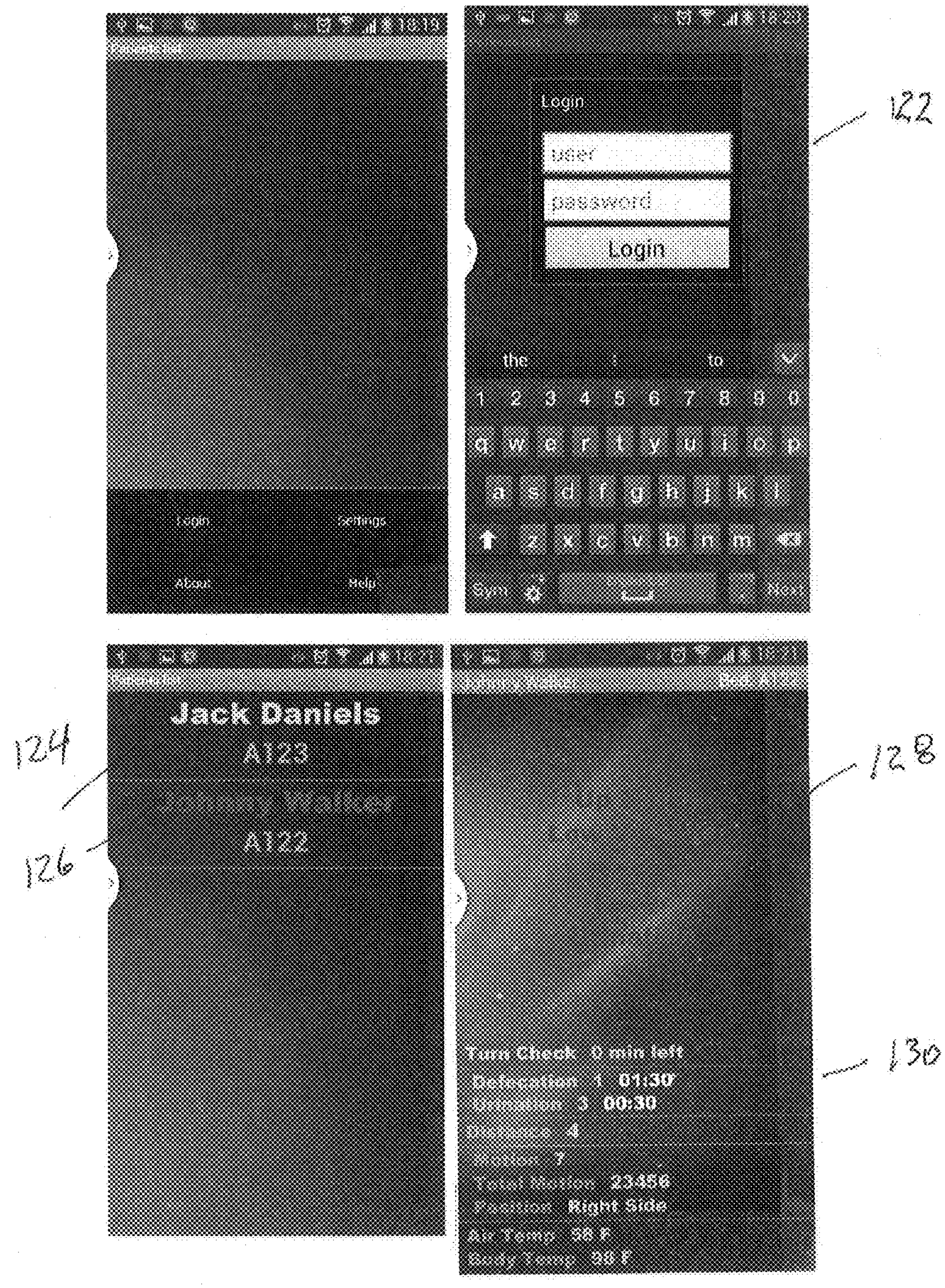

With reference to FIGS. 11 and 12, Nurse Pager P2, P3 may be an Android, or other operating system, smart phone 118 connected to Wi-Fi working with a custom smart phone application which converts it into a Nurse pager. Nurse receives alarms and data about her patients from server S2 or S3 and displays them on its screen 120 As a first step, smart phone 118 is configured as shown in the screenshot 120 in FIG. 11. When the Nurse logs in at screen 122, a list of patients 124 is displayed (FIG. 12). When pager 118 rings an alarm and the Nurse turns on her smart phone Pager 118, the patient with the alarm 126 flashes red. If the Nurse touches the alarm all data of that patient appears on screen 128. After the alarm is viewed and resolved by pressing Interface 12, 14 button B, the patient color returns to yellow. All data 130 about any patient is seen in real time on the screen by touching patient name.

The communication between D2 and T in I2 (FIG. 10) is identical to the first embodiment. Once the string of bits is received and checked it is memorized in an intermediary buffer to ensure no alarm is missed. This happens independently of Wi-Fi communication. Wi-Fi transmissions take place at equal times, once every 1 to 6 seconds for example. The moment Wi-Fi transmission comes up, data is taken from that buffer and transmitted through CV. If S2 confirms alarm reception then the buffer is reset. After an alarm is resolved, a nurse presses the button B" on I2 and I2 sends a package of data to server S2, so server S2 deactivates that alarm and displays in MA and in P2 that the alarm was resolved. Alarm is displayed in different colors in MA and in P2 on its different stages. The first stage and color is when an alarm was first received in server S2 from I2 and sent to P2. The second stage and next color is when an alarm is acknowledged by a nurse by touching the flashing patient name on her pager 118 (P2) screen. After that alarm is displayed on P2 the just received alarm refers to that patient. A flashing color occurs when a certain time passes without the alarm being resolved. The final color comes after the nurse resolves the alarm and presses the I2 button B". Then the alarm disappears from P2's screen. P3 is the same as P2.

The multisensory device 10 with the sensors described above, and central computer S2 suitably programmed, allows the caregivers and administrators to control the various functions of the system using the monitoring application (MA) shown in FIG. 19-32. In the first embodiment C does all calculations m Detector D1. In embodiments 2 and 3 the detector transmits temperature measurements from sensors to computer S2. In monitoring application table 200 the temperature rise limit and time, in which it occurs, are settable. Also all volumes and flows are calculated and recorded. Server S2 or S3 receives data from all interfaces and, by its monitoring application (MA—see FIG. 19), compares data with its settings. If data values received from the interfaces are equal to settings values prescribed in that table it sends alarms to nurse pagers 18. Server S2 may be only one computer with server software and monitoring application (MA) installed on it or it can be one computer working as server and a multitude of secondary computers PC, one in each facility section. Each computer PC has its own monitoring application MA installed. The system for one patient containing one D2, one I2 and a nurse pager P2 and a computer is preferred for homecare and has the advantage of recording all data about the patient with the possibility of medical staff to access these records online. Settings are prescribed by an operator in the monitoring application MA as the doctor recommends for each patient. These settings are written in a table on the computer screen. In this table 200 are, for example, incontinence features, Fall and Wandering features and Wound Management features.

The combination in the described system of incontinence detection by heat sensors together with position or orientation and motion, fall and wandering detection by accelerometer has a number of advantages. A large proportion of patients in hospital or nursing homes are both incontinent and bedridden. Incontinence detection and alarm is necessary to be associated with patients with wounds in Wound Management Turn Check because any wetness will aggravate the wound. Therefore combining position or orientation detection with wetness detection provides a more effective wound management. Detection of motion intensity in bed, agitation plus breath motions may assist in predicting an incontinence event and an incontinent patient infant or senior may be in greater danger of falling since the incontinent patient may try to reach a toilet. Preventing falls by an UP alarm followed by UP and Go alarm is therefore improved by also monitoring incontinent events. The association of incontinence detection and position or orientation/motion also assists in saving power at Detector 10. Transmission frequency depends on position and motion. When patient is in bed, transmissions for patient location are very rare. When patient position or orientation changes to stand up and the patient starts moving, transmission frequency for patient location increases with motion. As noted above, the orientation of the individual (lying down versus upright, on front, side or back position or orientation in bed) can influence temperature rise and the accuracy of the wetness detection, volume and flow detection at the incontinence sensor as can the ambient temperature. C can keep track of these variables and will adjust correspondingly. This combination of detections and measurements at all three sensors 28, 30, 32, Air temperature sensor 34 and ACC can therefore allow for corrections for a greater sensitivity and precision.

Figure 19:
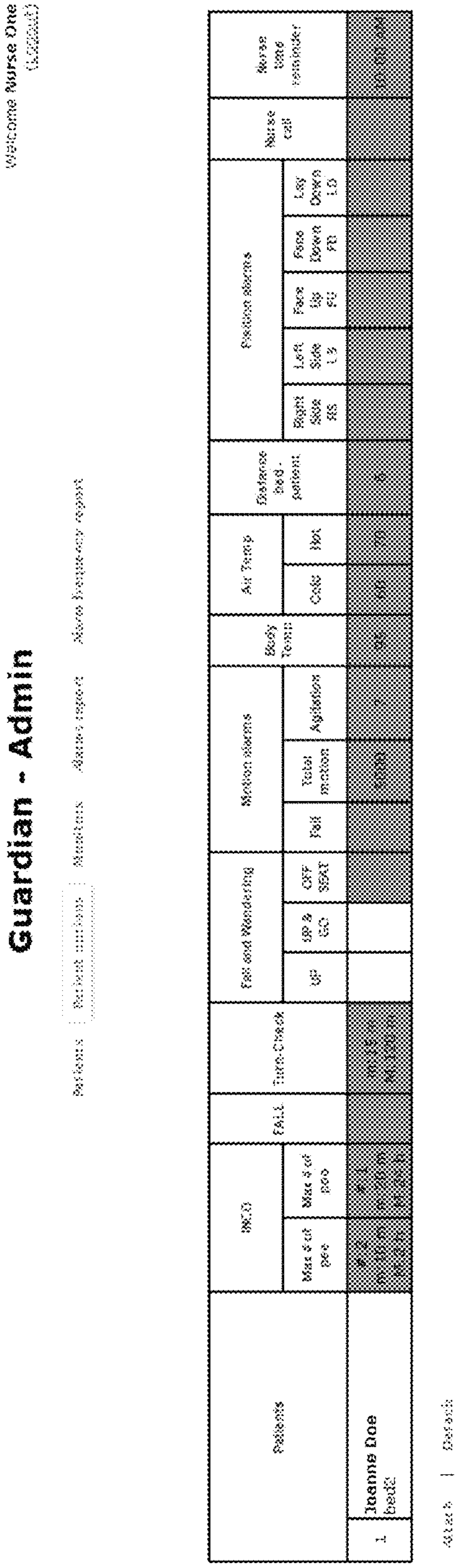
FIGS. 19-32 are screen shots of the monitoring application (MA) which controls the functions of the system, on the Doctor's and Nurse's systems respectively.
Figure 20:
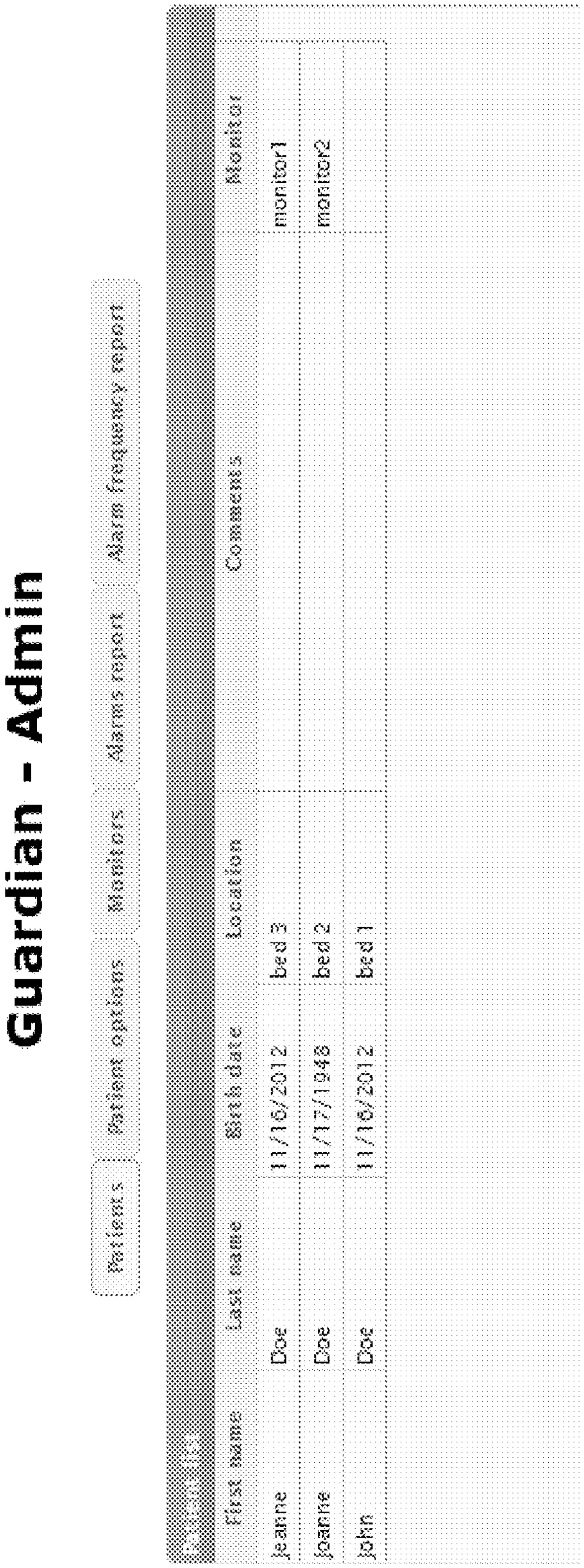
Figure 21:
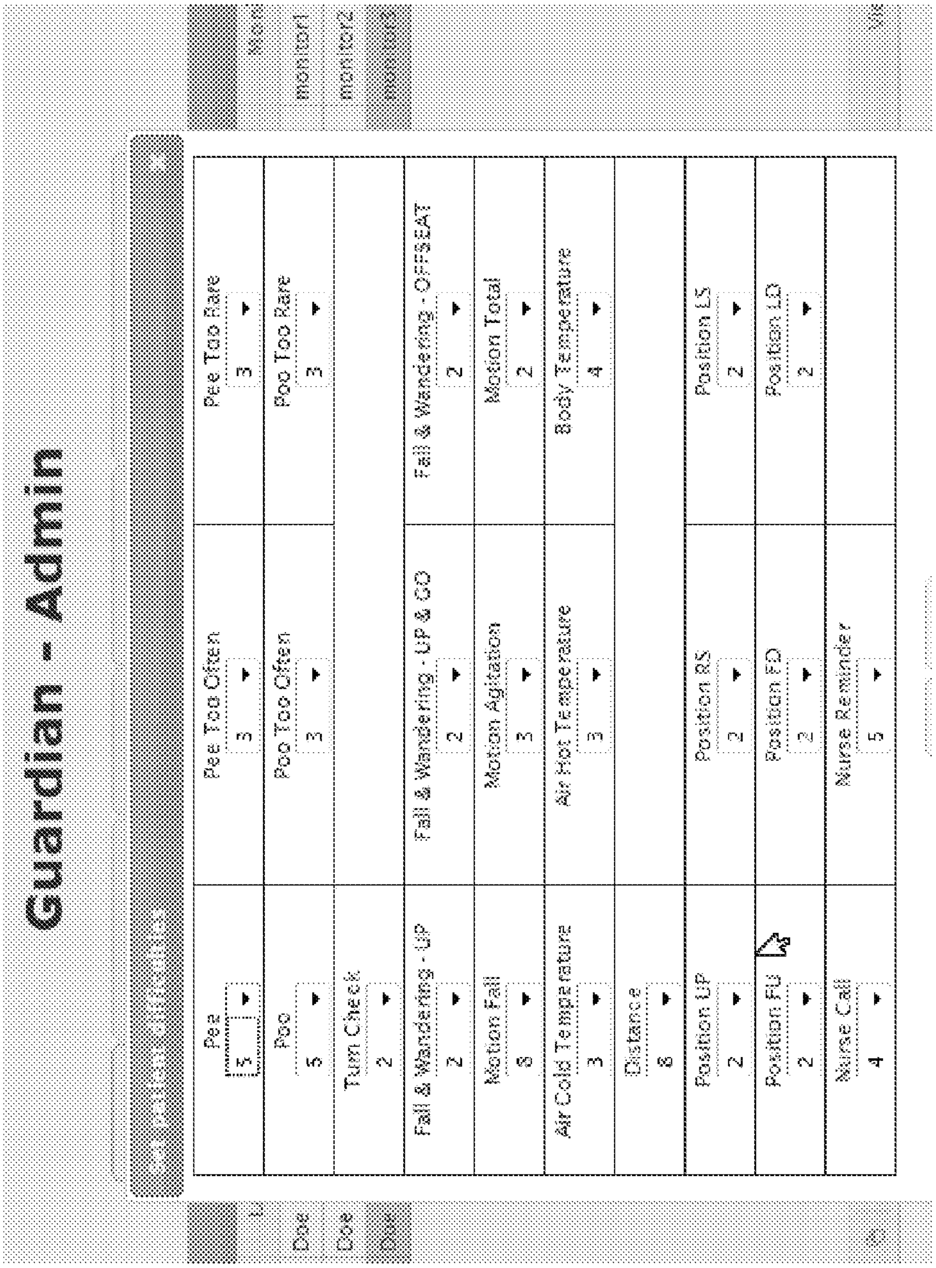
Figure 22:
Figure 23:
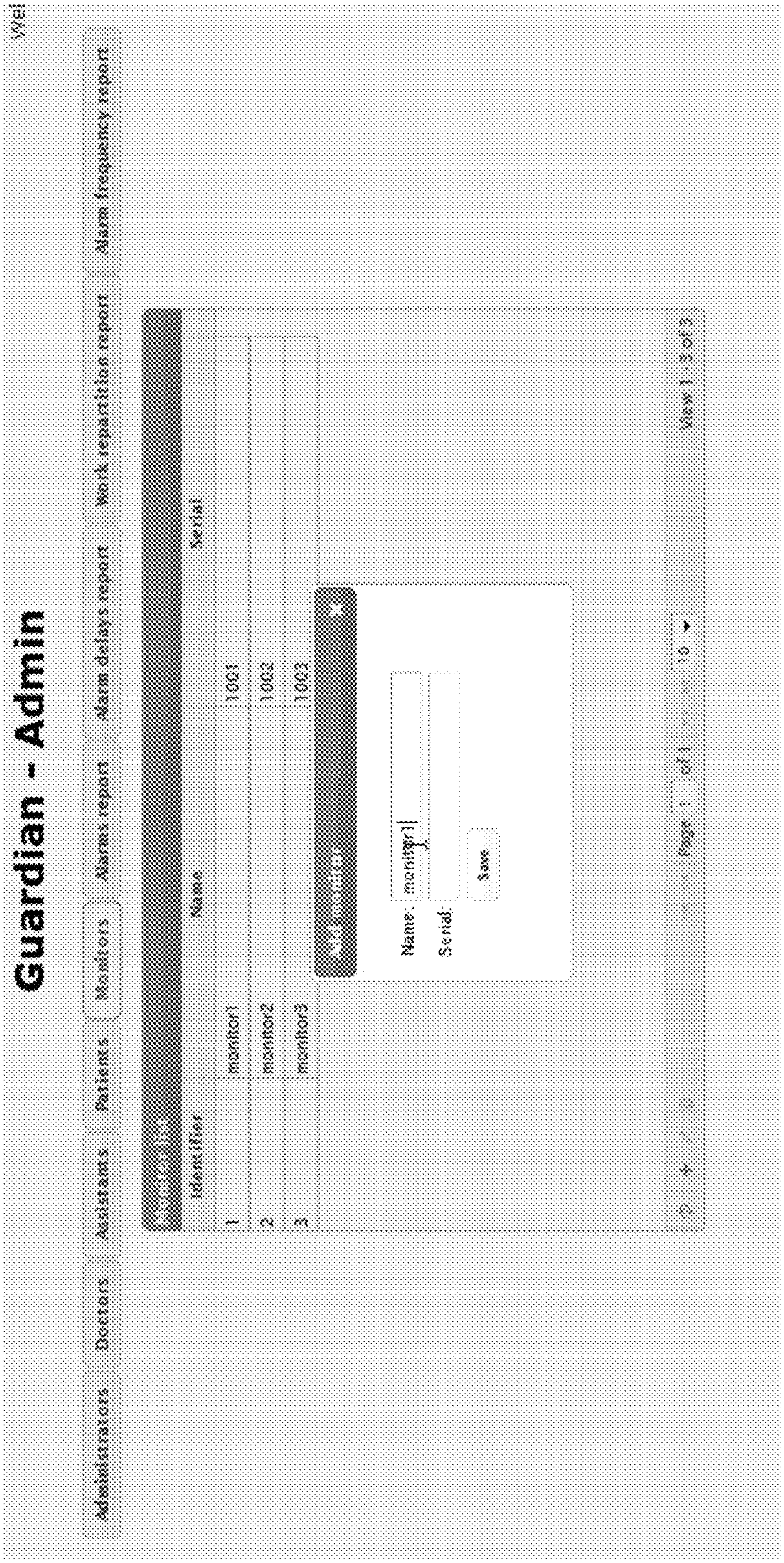
Figure 24:
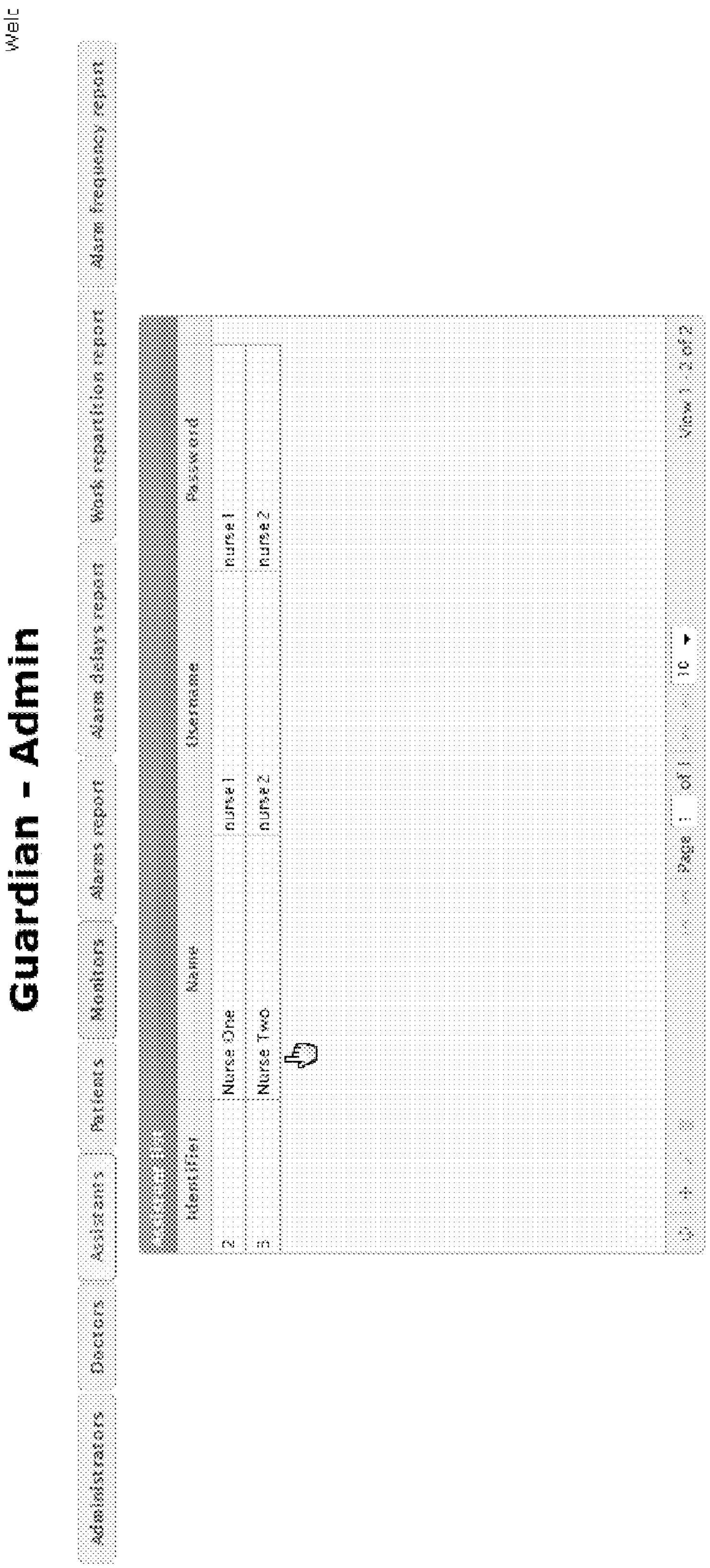
Figure 25:
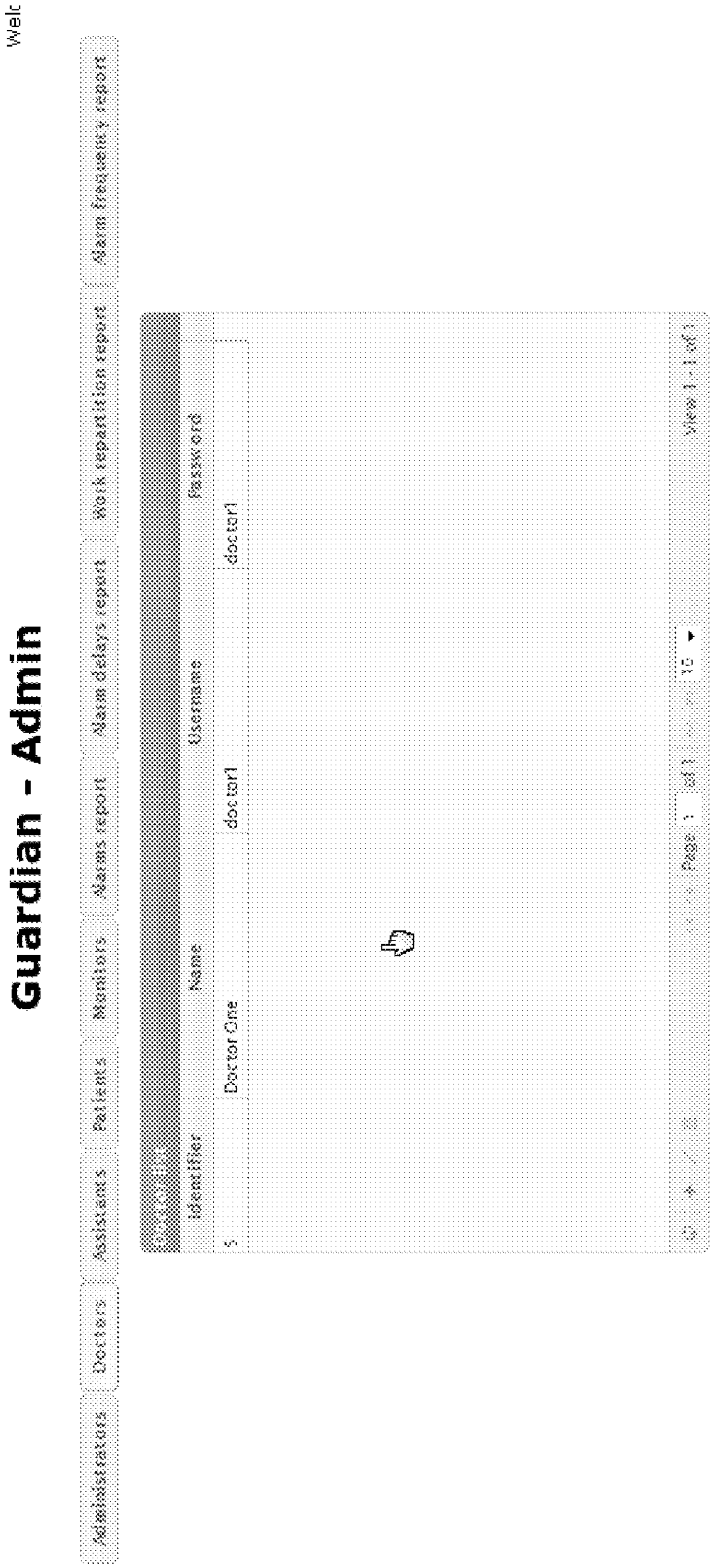
Figure 26:
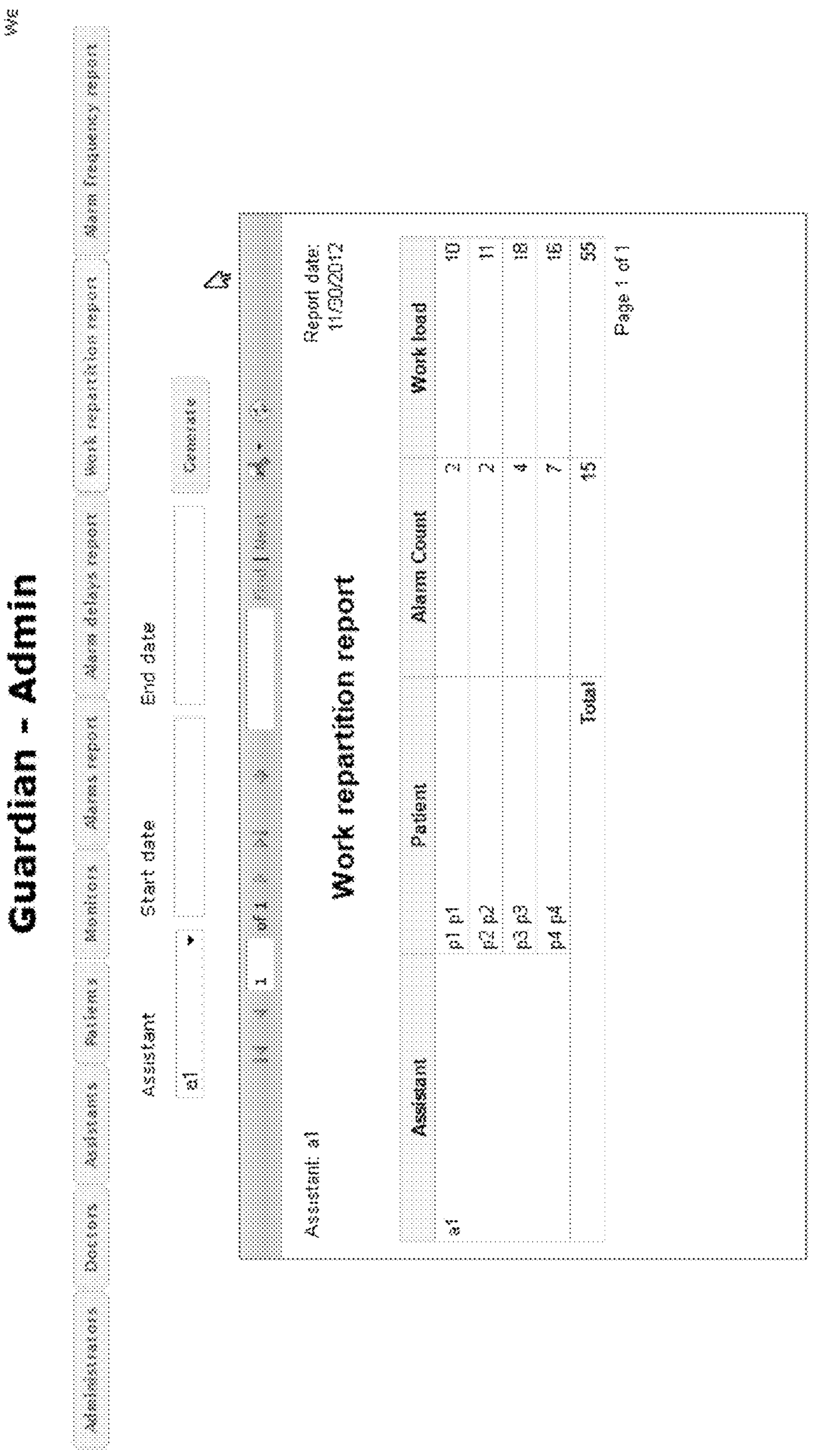
Figure 27:
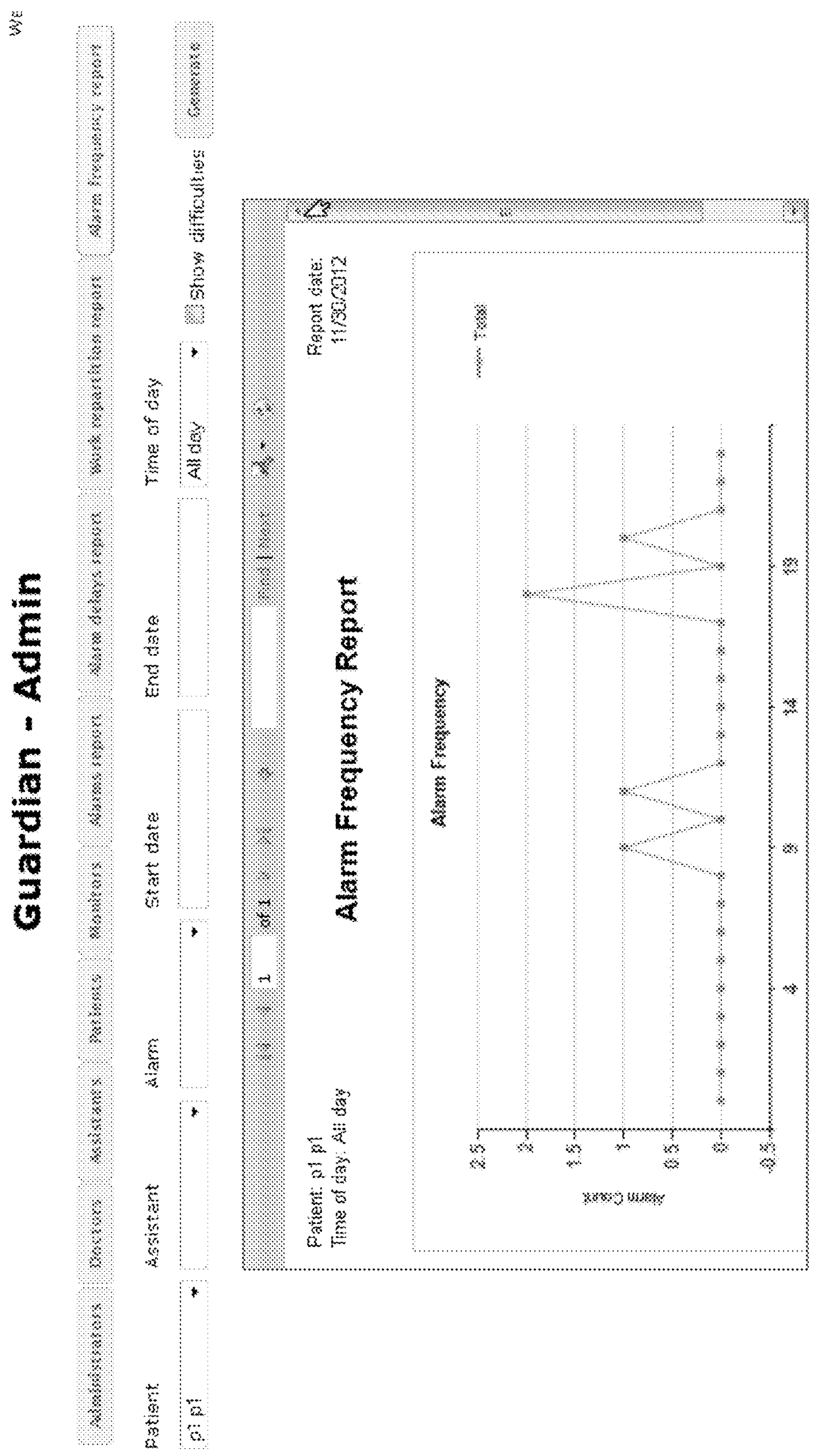
Figure 28:
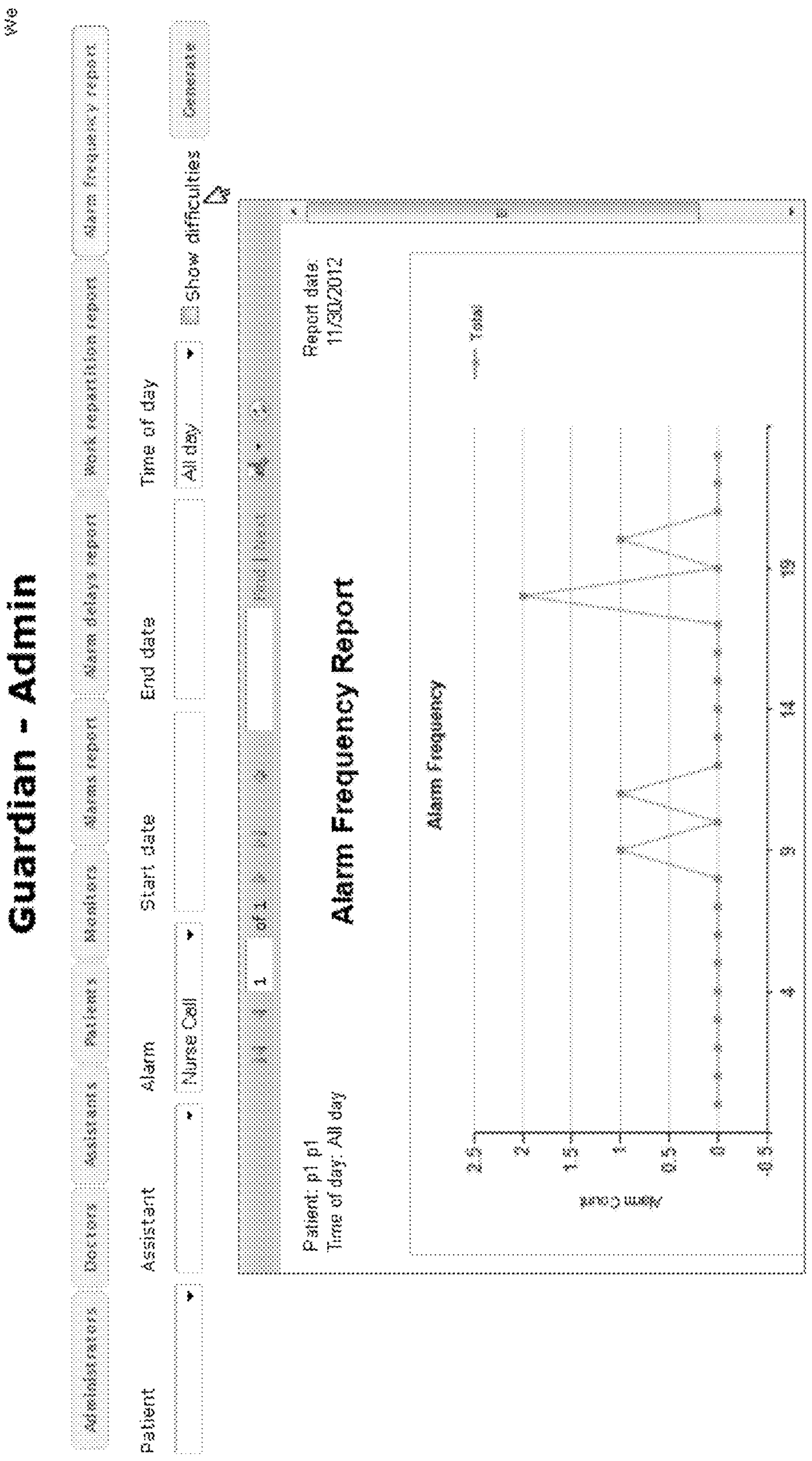
Figure 29:
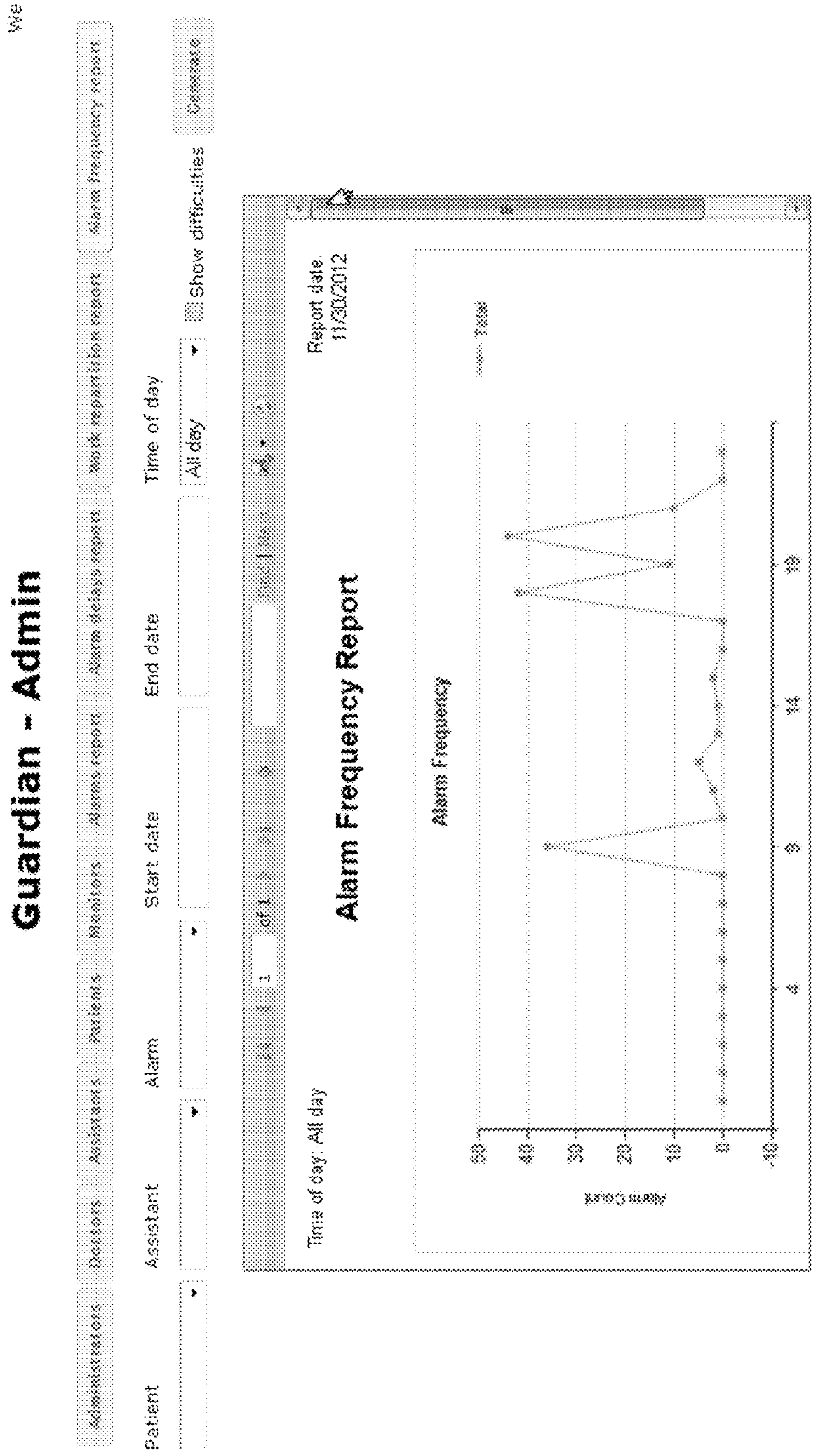
Figure 30:
Figure 31:
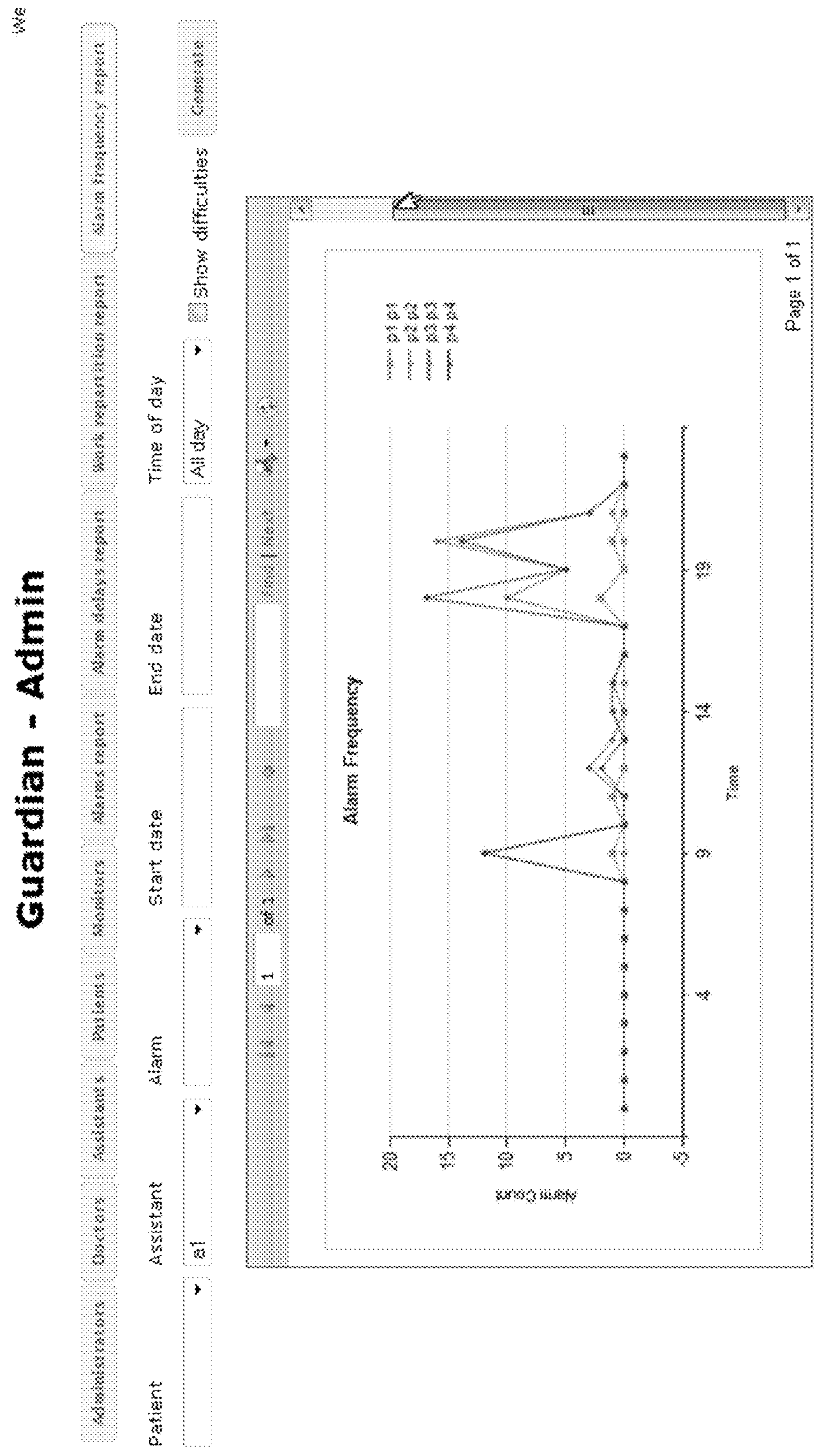
Figure 32:
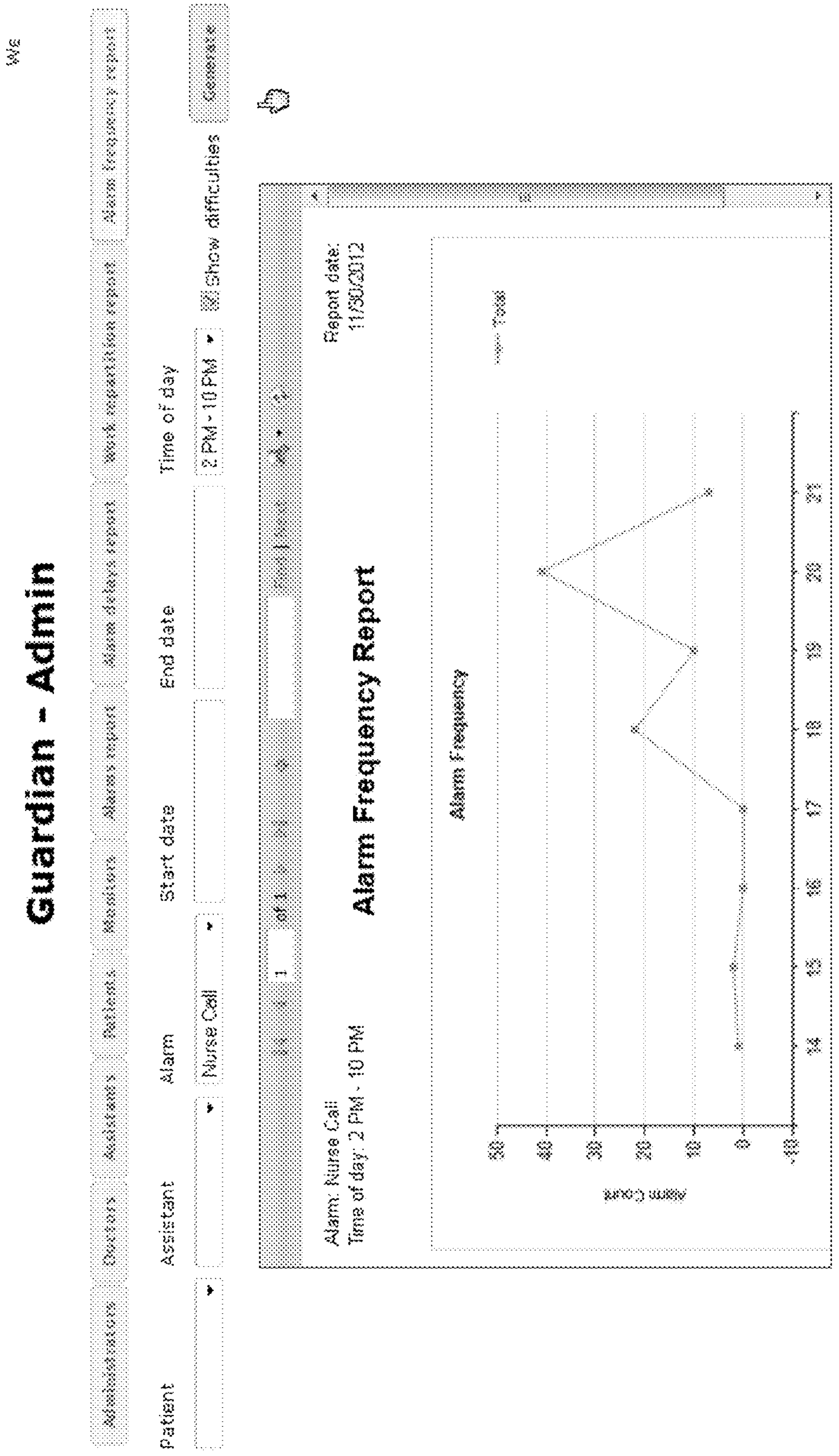

The features of the MA are illustrated in FIG. 19-32. Each assistant accesses a "Patient Options" page, from the assistant's home page, for each patient the assistant is responsible for, as shown in FIG. 19, in which the assistant can set the parameters for each variable which will trigger an alarm. The assistant maintains a list of his/her patients as in FIG. 20, with a record of each patient's location and monitor identification. Monitors can be added (FIG. 23). The level of difficulty which is assigned for that patient for the assistant to respond to each type of alarm event which the assistant mat need to deal with for that patient can be viewed or set as in FIG. 21. Doctors and assistants with access to the system are added, removed or viewed from the Administrator's home page (FIG. 24, 25) as can monitors 9FDog. 23. The Administrator is provided a report on all alarms generated by patients (FIG. 22). These can be viewed by time period and patient and by assistant. The Administrator can view an Alarm Delays Report (FIG. 31) showing the delay which occurred from the time of the alarm to the time of response by the assistant, selected by assistant, patient or time period. FIG. 26 illustrates a work repartition report which provides to the Administrator by assistant and time period the amount of work required for that assistant to respond to patient alarms. Alarm frequency reports are provided as a graph, selected by patient (FIG. 27), alarm type per patient (FIG. 28), by assistant (FIG. 31) and time of day (FIG. 29) and showing the sum of the level of difficulty of the alarms instead of numeric (FIG. 32).

Figure 13:
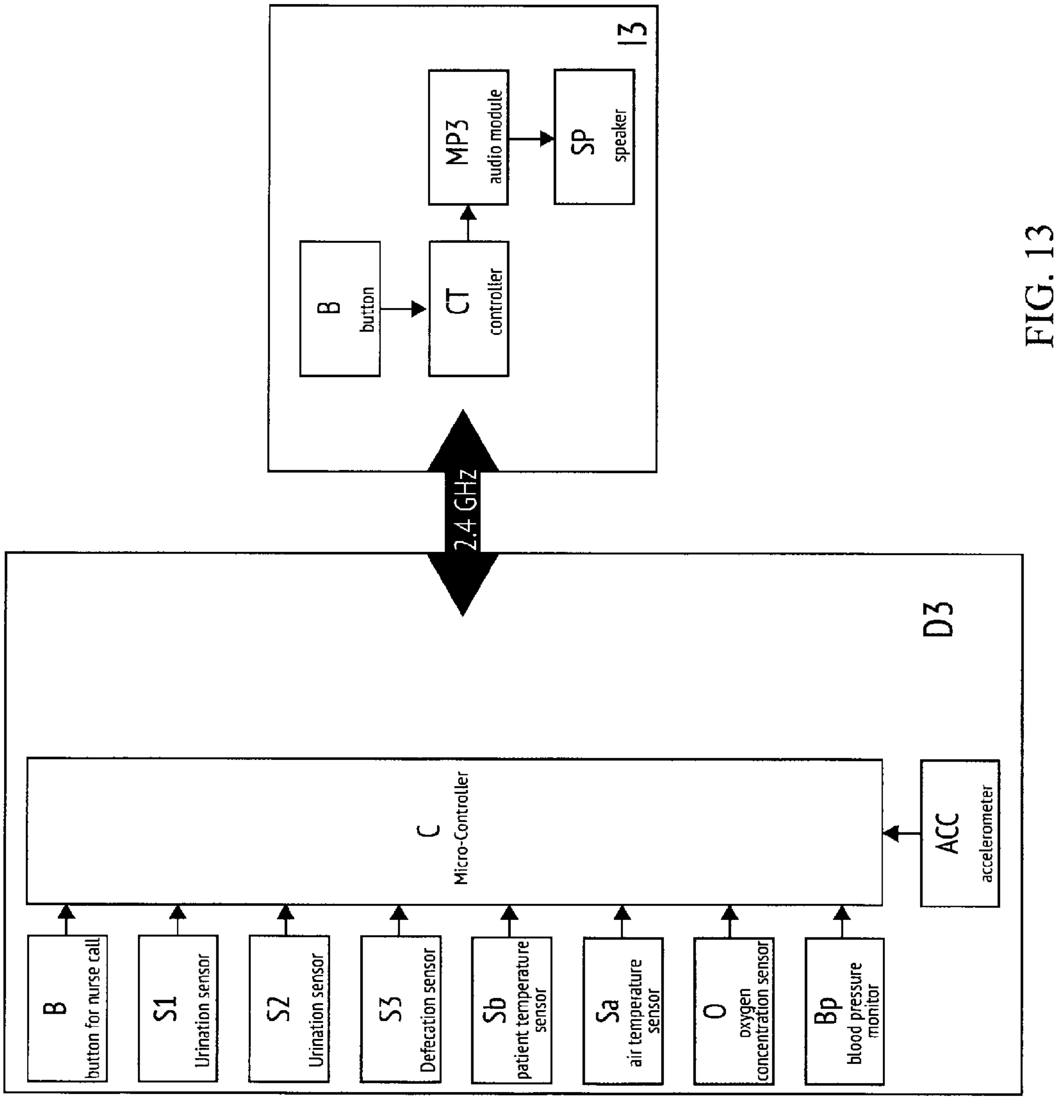
FIG. 13 is a schematic diagram illustrating the circuitry of the multisensory device and patient interface.
Figure 16:
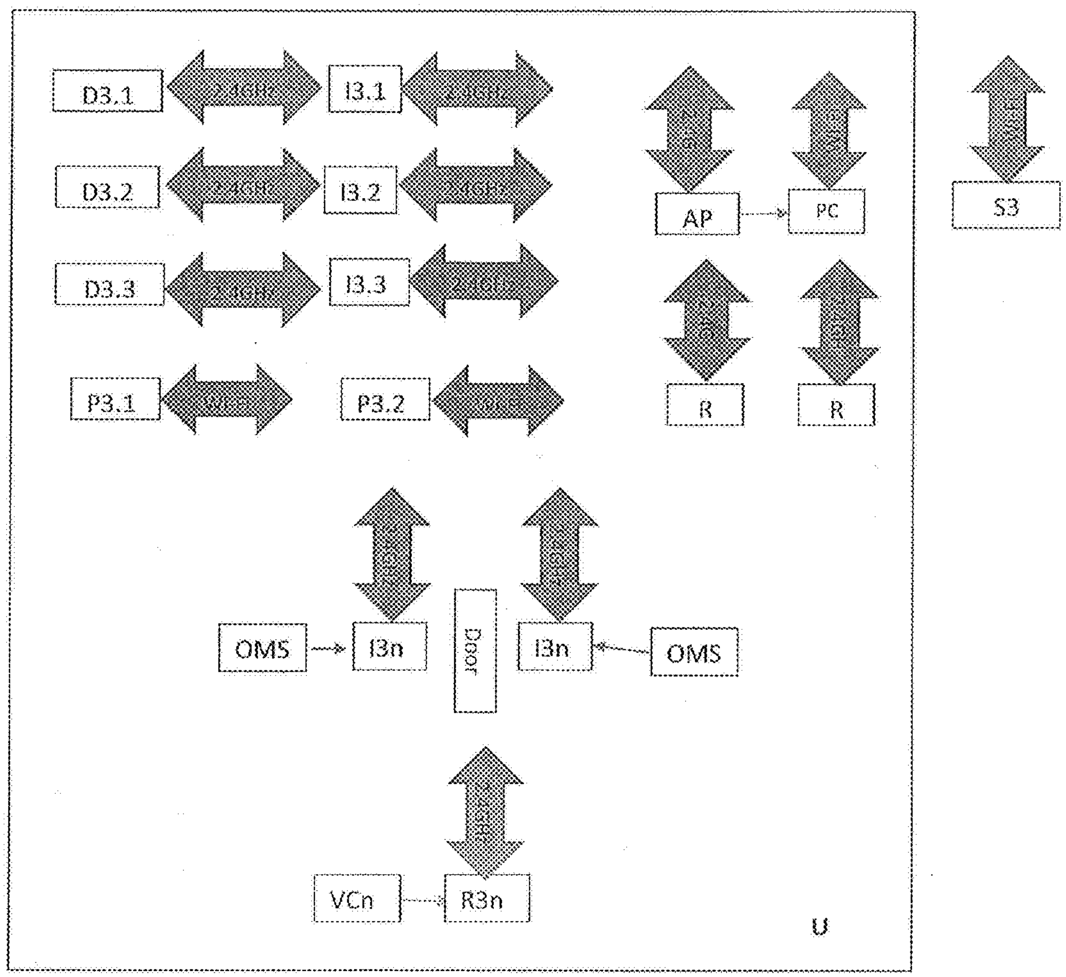
FIGS. 16-18 are schematic diagrams illustrating further embodiments of the communication system used in the invention.
Figure 17:
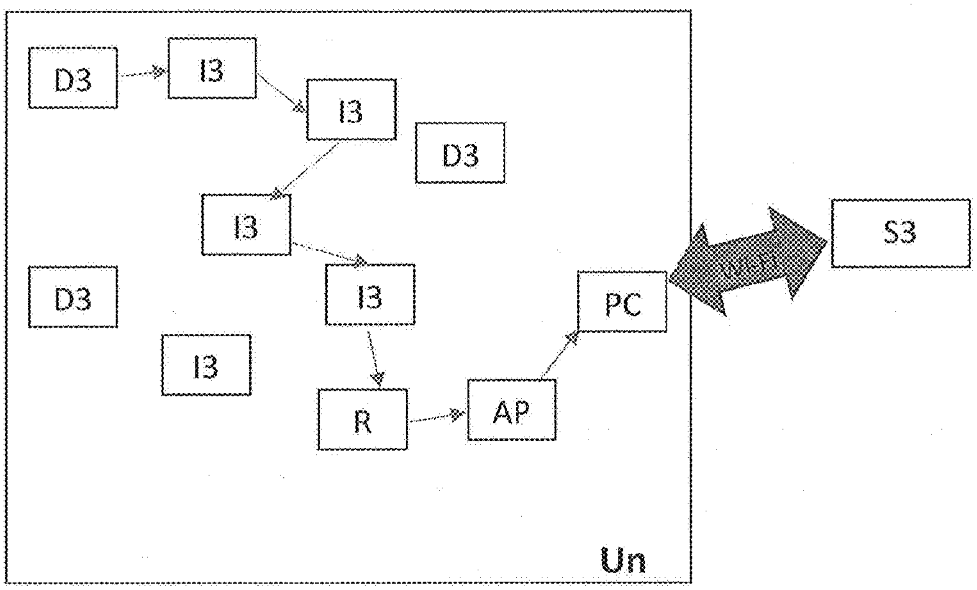
Figure 18:
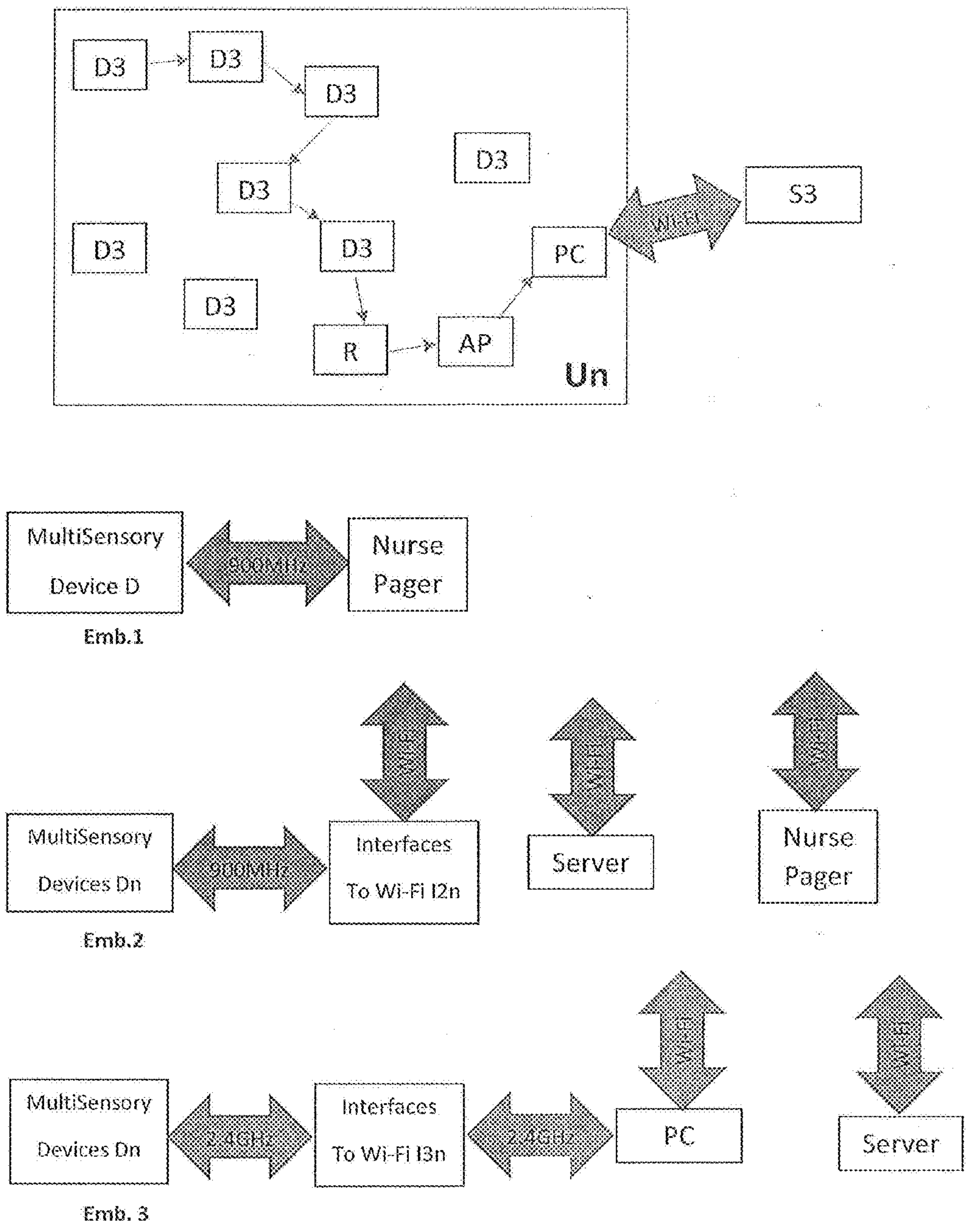

With reference to FIG. 16-18 a third embodiment 3 contains i) a multitude of units Un; ii) a multitude of access points AP connected to a multitude of PC's USB, connected to Wi-Fi; and iii) a server S3 similar to S2 and connected to Wi-Fi. A unit U contains: I) multitude of multi-sensory devices D3.*n* attached to the patient front on diaper or body, ii) a multitude of Interfaces I3.*n* located next to patient bed wall plugged in power; iii) an access point AP connected to a computer USB; iv) a computer PC connected to Wi-Fi; v) a multitude of Nurse Pagers P3 identical to P2. The circuits of D3 and I3 are shown in FIG. 13. D3's controller CT communicates with I3's controller CT by RF communication. Controller CT includes a microcontroller and a transceiver in the same housing.

D3 communicates with I3 by Zigbee protocol compliant to regulation IEEE 802.15.4. As illustrated in FIG. 17, data circulates from D3 and I3 to the next I3 and R until it arrives to AP. AP is connected to PC USB. A unit U communicates to a central server S3 through PC and Wi-Fi. PC works as a local server and has installed a Monitoring application MA as in the second embodiment. PC communicates to Wi-Fi and from there to pagers 118 (P3*n*) and institution server S3 or other computers. A unit may serve a healthcare facility section comprising multiple e.g. 1 to 20 pairs of devices 10 (D3) and interfaces I3 and one to 10 pagers 118 (P3). If a patient comes out of the reception range of interfaces I3 repeaters R are necessary. An R is an interface I3 without MP3 capability, SP and button B. Repeater R reports D3's location to the closest I3 or D3. If a patient's device 10 (D3) goes beyond the last I3, and I3 receives a weaker RF signal from D3, I3 orders D3 to increase its transmission strength. If reception is lost the last I3 or R generates an alarm. Always D3 transmission strength is optimized in order to save battery power, as currently applied for in cell phones. While D3 stays close to an I3 transmission strength is optimized as small as possible. By Zigbee protocol a patient location is thus always known by the closest Interface I3 or Repeater R. Therefore in this embodiment communication is assured no matter how many patients are in facility. Patient location is given by the closest I3 and it is displayed on MA and on P3.

The advantages of the second and third embodiments in FIG. 9 and FIG. 16-18 over the first embodiment are that one nurse takes care of more than 1 patient. Communication range is everywhere in a facility using its Wi-Fi. A Nurse sees continuously on her pager 118 all data about her patients. MA entries make possible the following. A dispatcher can supervise on computer S2 or S3 all alarms resolving. All data front devices 10 is processed safer and faster. Server S3 records and process all data. A manager can see and optimize each nurse's activities, which nurse work is harder or easier, which patient is easier or harder to care of. A Doctor can see each patient data and conclude about their health problems.

According to another variation of Embodiment 3 shown in FIG. 16, interfaces I3 can be dispensed with. In this case Turn-Check function does not have the ability (MP3 module) to wake up the patient. D3 can incorporate a vibrator or sound maker which can fulfill this function of waking up the patient.

According to yet another variation of Embodiment 3 shown in FIG. 16, if D3 contains an extra GPS module and a GPRS module they start to transmit to P3 data about patient and patient global position when patient is out of the RF Zigbee range as in D1.*a*. Communication by Zigbee protocol then stops. As a further variant, if D3 contains an extra Wi-Fi module it starts communicating with S3 and P3 through Wi-Fi when it is out of RF Zigbee range as in D1.*c*. Then communication by Zigbee protocol stops and D3 starts to communicate directly with in locations not covered by I3 or repeaters. Then when the patient comes out the area covered by Wi-Fi, the controller CT stops transmissions to Wi-Fi and starts GPS and GPRS modules. Since communication between D and P or I can be done through GPRS. In Embodiments 2 and 3, data can be transmitted to a nurse smart phone. A smart phone can play the role of server for all nurses and patients. And from smart phone to wifi and facility server. Data can be recorded in smart phone and/or in facility server. This way there is no limit to the communication range. If GPS is in D and location coordinates are transmitted through GPRS to nurse smart phone 118, the patient can be located wherever he is outside facility.

For record keeping there are multiple charts and recording possibilities in the system MA to assist facilities with managing staff as well as patients. All patient activity is recorded and stored indefinitely. This is useful to view daily activity as well as to record proof of care. Staff work load can be balanced by identifying needy patients and those less demanding. Daily activity clears by 24 hour periods. The administration computer 22 keeps complete records. In smaller facilities, day and long term records can be kept on the same computer and accessed by password.

Thus the present invention allows one nurse to handle more than one patient with one nurse receiving alarms from multiple patients, or it permits one detector/sensor to be exclusive to one nurse pager only. The system detects more than one urination or defecation in the same diaper, the system detects each urination and defecation separately in same diaper with reusable sensors since the sensors do not contact urine or feces inside diaper. The system measures urine and defecation quantity and flow. Frequency and number of incidents per patient and other patient data are recorded on administrative charts for later reference. A nurse is alerted as necessary, by sound and pager message, per the settings individually programmed for each patient. An alert sounds or is displayed on a nurse's pager if incidents are too frequent or too rare. This can show hidden patient problems like diarrhea, constipation, infection, prostate problems, diabetes, or cystitis.

The system can be used with less than all functions activated. It is suitable for a nursing home or a hospital, but also for homecare and for infants or pets. The system is useful for child monitoring, newborns, and youngsters, mentally challenged children and/or adults with propensity to wander. A simpler and less expensive system for home care use would includes only a Multi-sensory device 10 and a Pager P1. Customers can purchase the complete package or a single feature eg. Turn Check. Additional features can be purchased online, one at a time, by end user, and activated immediately when approval is granted by provider. Patient needs are programmed individually and activated/deactivated as health needs change.

Among the additional features which can be set and recorded in the MA are i) Body temperature alert, which measures patient body temperature and alerts nurse if fever, can be provided; Diaper wearer body temperature and fever; setup, alarm and display of said body temperature and fever; ii) Ambient temperature alert, which measures air temperature around patient and alerts if is cold or hot; Diaper wearer surrounding air temperature; setup, alarm and display of the air temperature; iii) Nurse Reminder of Patient appointments can be set in nurse's pager. v) The Nurse Call button on device D1 for patient use is provided, vi) Diaper wearer breath motion and non motion; alarm and display of said breath non motion. Breath count; Setup, alarm and display of said breath count; vii) Diaper wearer position when he or she lies in bed; setup, alarm and display of said position or orientation; Stand up position of diaper wearer and when it occurs; setup, alarm and display of said stand up position; Diaper wearer sit down position; display of said sit down position; viii) alarm if patient is in the process of rising from a seated position; Fall of diaper wearer; alarm and display of the fall; ix) Detect and display of stepping; stepping count, cadence and diaper wearer speed display; Diaper wearer run detection; alarm and setup; Distance walked or run; setup, alarm and display of said distance; Diaper wearer speed; display of said speed; Direction walked or run; Setup, alarm and display of said direction; Diaper wearer movement intensity; display of said intensity; setup and alarm if said intensity and timing when it occurs; x) Diaper wearer presence in a certain perimeter with a settable alarm radius. Setup, alarm and display of said perimeter; Diaper wearer passing through certain doors and passing direction. Setup, alarm and timing when it occurs; Distance between diaper wearer and attendant pager. Display of said distance; Diaper wearer global position. Display and alarm; xi) Oxygen content in blood; setup, display and alarm of said oxygen content; Pulse detection and count, display and alarm; Blood pressure, display and alarm; xii) Diaper wearer video display on said Pager display, on PC monitor, on Internet and on mobile phone.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

What is claimed is:

1. A system for monitoring one or a plurality of patients each wearing an absorbent article for controlling incontinence comprising:

i) a plurality of temperature sensors for removable attachment to the outer surface of said absorbent article, each at a separate defined location on said outer surface of said absorbent article and external to said absorbent article and in contact with said outer surface of said absorbent article, each said temperature sensor generating a signal indicative of temperature measurement of said outer surface of said absorbent article at each said separate defined location, said plurality of temperature sensors thereby generating a plurality of signals indicative of said temperature measurements of said outer surface of said absorbent article at said separate defined locations;

ii) means for communicating said plurality of signals indicative of temperature measurement of said outer surface of said absorbent article at said separate defined locations to a processor;

iii) wherein said processor is provided with computer code which, when executed, determines based upon said plurality of signals indicative of temperature measurements of said outer surface of said absorbent article at said plurality of separate defined locations whether a urination or defecation event has occurred in said absorbent article; and iv) means for communicating the occurrence of said event to a care-giver.

2. The system of claim 1 further comprising an accelerometer for providing a signal indicative of a change in motion, position or orientation of said absorbent article, and means for communicating said signal indicative of a change in motion, position or orientation to said processor.

3. The system of claim 2 further comprising a temperature sensor for providing a signal indicative of said patient's body temperature.

4. The system of claim 3 further comprising a temperature sensor for providing a signal indicative of the ambient air temperature adjacent to said absorbent article.

5. The system of claim 4 for monitoring one or a plurality of patients, further comprising a plurality of displays.

6. The system of claim 1 wherein said temperature sensors are connected electrically to said processor.

7. The system of claim 2 wherein said accelerometer comprises a three axis accelerometer connected electrically to an amplifier and communicating with said processor by a radio transmitter or a radio transceiver.

8. A system as claimed in claim 2 further comprising a global positioning device communicating with said processor.

9. The system of claim 8 further comprising one or more additional sensors each communicating with said processor and selected from the group consisting of a body temperature sensor, air temperature sensor, reflective pulse oximeter, a blood pressure meter and a pulse detector.

10. An absorbent article for use in a system for monitoring incontinence events, comprising:

i) a plurality of temperature sensors for removable attachment to the outer surface of said absorbent article, each at a separate defined location on said outer surface of said absorbent article and external to said absorbent article and in contact with said outer surface of said absorbent article and each generating a first signal indicative of temperature measurement of said outer surface of said absorbent article at each said separate defined location at each of said plurality of temperature sensors;

ii) an accelerometer for providing a second signal indicative of a change in motion, position or orientation of said absorbent article;

iii) means for communicating said plurality of first signals and said second signal to a processor; and iv) processing means for determining from said temperature measurements whether a urination or defecation event has occurred, calculating a change in position or orientation or motion of said absorbent article and generating third and fourth signals indicative thereof.

11. A method of detecting and evaluating an incontinence event in a patient wearing an absorbent incontinence garment, comprising:

i) providing a plurality of temperature sensors for attachment to the outer surface of said garment at spaced locations on said outer surface of said garment and external to said garment and in contact with said outer surface of said garment, each of said plurality of temperature sensors generating a signal indicative of the temperature of said outer surface of said garment at said spaced locations;

ii) attaching said plurality of temperature sensors at said spaced locations, on said outer surface of said garment each generating a signal, said plurality of temperature sensors thereby providing a first plurality of signals indicative of multiple temperature readings of said outer surface of said garment at said spaced locations;

iii) communicating said first plurality of signals to a processor;

iv) using said multiple temperature readings to determine whether a urination or defecation event has occurred in said garment based on the location of the sensor and the rate of temperature increase at the sensor;

v) communicating and displaying said event to a caregiver.

12. The method of claim 11 further comprising the steps of vi) providing an accelerometer for attachment to said garment at a specified location for generating a second signal indicative of a change in position or orientation or motion of said garment gannent; and vii) communicating said second signal to said processor.

13. The method of claim 12 wherein said second signal is indicative of the acceleration, position and/or orientation of said garment, and using said indication of said acceleration, position and/or orientation of said garment in addition to said multiple temperature readings to communicate and display said event to said caregiver.

14. The method of claim 12 further comprising the step of said processor determining the garment's position or orientation to determine whether the patient wearing the garment requires attention.

15. The method of claim 14 further comprising the step of said processor determining the ambient air temperature to determine whether the patient wearing the garment requires attention.

16. The method of claim 15 further comprising the step of monitoring the motion of said garment for wound check to determine whether the patient wearing the garment requires attention.

* * * * *